United States Patent
Hattori et al.

[11] Patent Number: 5,995,136
[45] Date of Patent: Nov. 30, 1999

[54] FRAME SEQUENTIAL TYPE IMAGING APPARATUS FOR OBTAINING HIGH RESOLUTION OBJECT IMAGE BY IRRADIATING FRAME SEQUENTIAL LIGHT ON THE OBJECT, PHOTOELECTRICALLY CONVERTING THE OBJECT IMAGE AND PROCESSING SIGNALS BY A SOLID STATE IMAGING DEVICE

[75] Inventors: Shinichiro Hattori, Akishima; Masahide Kanno, Hachioji; Akira Hasegawa, Akishima, all of Japan

[73] Assignee: Olympus Optical Co., Ltd., Tokyo, Japan

[21] Appl. No.: 08/357,269

[22] Filed: Dec. 13, 1994

Related U.S. Application Data

[63] Continuation of application No. 08/059,534, May 12, 1993, abandoned.

[30] Foreign Application Priority Data

May 13, 1992 [JP] Japan ..................... 4-120822
Jul. 16, 1992 [JP] Japan ..................... 4-189657

[51] Int. Cl.$^6$ ................ H04N 7/18; H04N 9/04
[52] U.S. Cl. ................ 348/70; 348/269; 348/273; 348/337; 348/340
[58] Field of Search ............. 348/65, 68, 69, 348/70, 268, 269, 270, 271, 272, 273, 274, 275, 276, 277, 278, 279, 280, 335, 337, 340, 342

[56] References Cited

U.S. PATENT DOCUMENTS

| | | |
|---|---|---|
| 3,922,069 | 11/1975 | Kishikawa et al. . |
| 4,009,941 | 3/1977 | Verdijk et al. . |
| 4,605,956 | 8/1986 | Cok . |
| 4,626,897 | 12/1986 | Sato et al. . |
| 4,882,619 | 11/1989 | Hasegawa et al. . |
| 4,897,537 | 1/1990 | Miyamoto et al. ............. 359/389 |
| 4,920,418 | 4/1990 | Robinson ................ 358/213.28 |
| 4,967,264 | 10/1990 | Parulski et al. ............... 358/44 |
| 5,006,928 | 4/1991 | Kawajiri et al. ............. 358/98 |
| 5,216,512 | 6/1993 | Bruijns et al. .............. 358/225 |

FOREIGN PATENT DOCUMENTS 46-36372 of 1971 Japan ..................... 358/47

*Primary Examiner*—Bryan Tung
*Attorney, Agent, or Firm*—Armstrong, Westerman, Hattori, McLeland & Naughton

[57] ABSTRACT

An electronic endoscope apparatus serving as a frame sequential type imaging apparatus comprises an electronic endoscope for picking up an object, a CCU for driving and controlling the electronic endoscope and processing imaging signals originated from the electronic endoscope, and a high resolution monitor displaying video signals processed by the CCU. An imaging optical system is provided at the tip of the electronic endoscope to receive reflected light irradiated on an object. The imaging optical system is provided with specific wavelength optical path changing apparatus for shifting an optical path of reflected light of a predetermined wavelength range between an objective lens system and a CCD. The specific wavelength optical path changing apparatus is a plate glass which transmits frame sequential light reflected from an object through the objective lens system. A surface of the plate glass facing CCD is bisected in two and coated with a first transmission filter and second transmission filter having different transmission characteristics. From among R, G1, G2, and B regions, the first transmission filter transmits the light of R, G1, and B regions and the second transmission filter transmits the light of R and G2 regions. The second transmission filter shifts an optical axis of the transmitted light.

43 Claims, 22 Drawing Sheets

FIG.7(a)

| R-1/1 | R-2/1 | R-3/1 |
|-------|-------|-------|
| R-1/2 | R-2/2 | R-3/2 |
| R-1/3 | R-2/3 | R-3/3 |

FIG.7(b)

| G1-1/1 | G1-2/1 | G1-3/1 |
|--------|--------|--------|
| G1-1/2 | G1-2/2 | G1-2/2 |
| G1-1/3 | G1-2/3 | G1-3/3 |

FIG.7(c)

| G2-1/1 | G2-2/1 | G2-3/1 |
|--------|--------|--------|
| G2-1/2 | G2-2/2 | G2-3/2 |
| G2-1/3 | G2-2/3 | G2-3/3 |

FIG.7(d)

| B-1/1 | B-2/1 | B-3/1 |
|-------|-------|-------|
| B-1/2 | B-2/2 | B-3/2 |
| B-1/3 | B-2/3 | B-3/3 |

FIG.22(a)

| R-1/1 | R-2/1 | R-3/1 |
|-------|-------|-------|
| R-1/2 | R-2/2 | R-3/2 |
| R-1/3 | R-2/3 | R-3/3 |

FIG.22(b)

| G-1/1 | G-2/1 | G-3/1 |
|-------|-------|-------|
| G-1/2 | G-2/2 | G-3/2 |
| G-1/3 | G-2/3 | G-3/3 |

FIG.22(c)

| B-1/1 | B-2/1 | B-3/1 |
|-------|-------|-------|
| B-1/2 | B-2/2 | B-3/2 |
| B-1/3 | B-2/3 | B-3/3 |

FIG.23(a) CLK0
FIG.23(b) CLK1
FIG.23(c) CLK2
FIG.23(d) R FRAME MEMORY OUTPUT
FIG.23(e) BUFFER 49a OUTPUT
FIG.23(f) BUFFER 49b OUTPUT

FRAME SEQUENTIAL TYPE IMAGING APPARATUS FOR OBTAINING HIGH RESOLUTION OBJECT IMAGE BY IRRADIATING FRAME SEQUENTIAL LIGHT ON THE OBJECT, PHOTOELECTRICALLY CONVERTING THE OBJECT IMAGE AND PROCESSING SIGNALS BY A SOLID STATE IMAGING DEVICE

This application is a continuation of application Ser. No. 08/059,534 filed May 12, 1993, now abandoned.

BACKGROUND OF THE INVENTION

1. Field of the Invention

The present invention relates to a frame sequential type imaging apparatus in which frame sequential light is irradiated on an object and an object image is photoelectrically converted and picked up by a solid state imaging device.

2. Description of the Related Art

Several kinds of frame sequential type imaging apparatuses which irradiate frame sequential light on an object and which photoelectrically convert and pick up an object image have been proposed.

A solid state imaging device used in these frame sequential type imaging apparatuses is composed of a plurality of picture elements for imaging. The imaging resolution by means of a solid state imaging device is largely affected by the number of the picture elements for imaging.

Recent integration technology has brought about increases in the number of the picture elements for imaging and improvement in imaging resolution resulting in an increase in the demand for high resolution in an object image display.

In such a condition, in order to substantially improve the imaging resolution by imaging devices, it has been recently proposed that an imaging element is vibrated by ½ pitch of a picture element interval perpendicularly to an optical path by piezoelectrics or the like, or that an object image formed on an imaging surface of an imaging device is shifted by ½ pitch of a picture element interval by providing a vibrating prism on an optical path, or that an optical axis of incident light is shifted by an optical system to shift ½ pitch of a picture element interval of an object image on a forming image device.

However, a driving means, such as piezoelectrics, is needed to vibrate a prism placed in an imaging device or on an optical path. For example, in a case of limited space, such as a tip portion of an electronic endoscope which is one of frame sequential type imaging apparatuses, driving means cannot be attached to the tip portion, or even if attached, there has been inconvenience such that the tip shape becomes larger.

Also, there has been a problem of effect on mechanical durability of an apparatus by vibration of driving means, although the problem is not limited to an electronic endoscope.

Further, in a conventional type which optically shifts an optical axis of an incident light, incident light has a plurality of wavelength ranges and all of the optical axes of the light of the wavelength ranges are shifted, so that an object image on a forming image device is shifted. Therefore, an optical system in which all optical axes are shifted for all light in every wavelength range is needed. Thus, there is a problem in which the construction of the optical system is complicated.

SUMMARY OF THE INVENTION

An object of the present invention is to provide a frame sequential type imaging apparatus which has a simple construction and optically moves an optical path of a specific wavelength range, so that the apparatus can pick up an image of an object with high resolution.

Another object of the present invention is to apply the aforesaid frame sequential type imaging apparatus to an electronic endoscope apparatus or a microscope.

The frame sequential type imaging apparatus of the present invention comprises irradiating means for irradiating light on an object, image pick-up means for sequentially picking up an observed image of the object in three or more of a plurality of wavelength ranges by light emitted by the irradiating means, and image forming position changing means for forming an observed image picked up by the image pick-up means in at least two wavelength ranges in a same position of the plurality of wavelength ranges in the same position of wavelength ranges on an imaging surface of the image picking up means, and for forming an observed image in at least one of the remainder of the plurality of wavelength ranges in a position different from the same position.

The other characteristics and advantages of the present invention will be sufficiently apparent from the following explanation.

BRIEF DESCRIPTION OF THE DRAWINGS

FIGS. 1 to 11 relate to the first embodiment;

FIG. 1 is a diagram showing construction of an electronic endoscope serving as a frame sequential type imaging apparatus;

FIG. 2 is a diagram showing construction of an imaging optical system;

FIG. 3 is a spectral transmission characteristics diagram showing characteristics of a transmission filter;

FIG. 4 is a diagram showing construction of a rotary filter;

FIG. 5 is a diagram showing construction of a signal processing circuit;

FIG. 6 is an illustration explaining an imaging state of a CCD;

FIG. 7 is an illustration explaining an example of a storage format of image information in a frame memory;

FIG. 8 is a timing chart explaining image readout by a signal processing circuit;

FIG. 9 is an illustration explaining picture elements on an imaging surface of a CCD;

FIG. 10 is an illustration explaining an interpolation method of image information on a high resolution monitor;

FIG. 11 is a diagram showing construction of an example of transformation of a rotary filter;

FIG. 14 is a diagram showing construction of specific wavelength optical path changing means;

FIG. 15 is a reflection characteristic diagram showing reflecting filter characteristics;

FIG. 16 is a diagram showing construction of a tip portion of a forward-viewing type electronic endoscope apparatus serving as a frame sequential type endoscope apparatus;

FIG. 17 is a diagram showing construction of a tip portion of a side-viewing type electronic endoscope apparatus serving as a frame sequential type endoscope apparatus;

FIGS. 19 to 25 relate to the sixth embodiment;

FIG. 19 is a diagram showing construction of a rotary filter;

FIG. 20 is a diagram showing construction of a signal processing circuit;

FIG. 21 is an illustration explaining an imaging state of a CCD;

FIG. 22 is an illustration explaining an example of a storage format of image information at a frame memory;

FIG. 23 is a timing chart explaining image readout by a signal processing circuit;

FIG. 24 is an illustration explaining picture elements on an imaging surface of a CCD;

FIG. 25 is an illustration explaining an interpolation method of image information on a high resolution monitor;

FIG. 26 is a diagram showing construction of an imaging optical system of a frame sequential type imaging apparatus;

FIG. 27 is a sectional view on each axis in FIG. 21;

FIG. 28 is an illustration explaining color shifting on a high vision monitor.

DETAILED DESCRIPTION OF THE PREFERRED EMBODIMENTS

Figure 1:
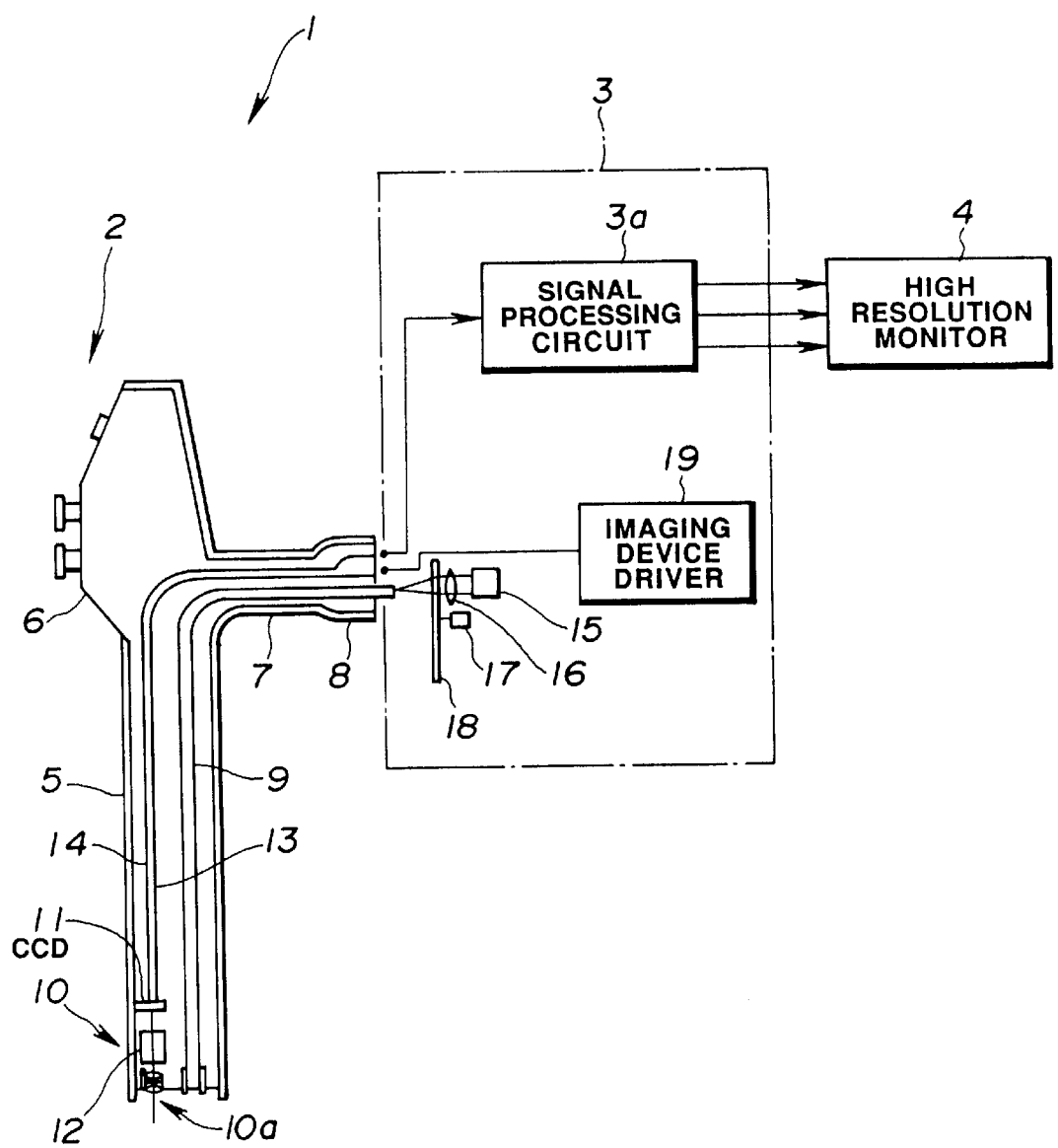

As shown in FIG. 1, an electronic endoscope apparatus 1 serving as a frame sequential type imaging apparatus of the first embodiment comprises an electronic endoscope 2 picking up an image of an obJect, a camera control unit (hereinafter, CCU) 3 driving and controlling the electronic endoscope 2 and processing imaging signals from the electronic endoscope 2, and a high resolution monitor 4 displaying video signals processed by the CCU 3.

The electronic endoscope 2 has an elongated and, for example, flexible insertion tube 5. A wide diameter operation portion 6 is attached to the distal end of the insertion tube 5. From the distal end of the operation portion 6, a flexible universal cord 7 is extended in the side direction. The connector 8 is provided at the tip portion of the universal cord 7. The universal cord 7 is connected to the CCU 3 through the connector 8.

In the insertion tube 5, a light guide 9 for transmitting illuminating light is inserted. The tip surface of the light guide 9 is provided at the tip of the insertion tube 5 and can emit illuminating light in the forward direction of the tip. The incident end of the light guide 9 is connected to the connector 8 through the universal cord 7.

In order to receive reflected light emitted from the emitting end surface of the light guide 9, an imaging optical system 10 is provided adjacent to the emitting end of the light guide 9. The imaging optical system 10 comprises an objective lens system 10a and a solid state imaging device, such as a CCD 11 which is arranged in the image forming position of the objective lens system 10a. The CCD 11 has sensitivity in a wide wavelength range including the visible region and extending from an ultraviolet range to an infrared range. Specific wavelength optical path changing means 12 for shifting a predetermined wavelength, such as an optical path of reflected light of a G2 wavelength range described below, is provided between the objective lens system 10a and the CCD 11.

Signal lines 13 and 14 are connected to the CCD 11 and further connected to the connector 8 through the insertion tube 5 and universal cord 7.

A lamp 15 emitting light of a wide band extending from, ultraviolet to the infrared is provided in the CCU 3. A general Xenon lamp and strobe lamp can be used as the lamp 15. The Xenon lamp and strobe lamp emit not only visible light but also a large quantity of ultraviolet light and infrared light. Electricity is supplied to the lamp 15 by a power source (not illustrated). A condenser lens 16 condensing light from the lamp 15 on the incident end surface of the light guide 9 is provided in the forward direction of the lamp 15. A rotary filter 18 is provided between the condenser lens 16 and the incident end surface of the light guide 9. The rotary filter 18 is rotated and driven by a motor 17 which makes illuminating light from the lamp 15, frame sequential light of a predetermined wavelength range, such as R region, G1 region, G2 region and B region. These regions are explained below.

In the CCU 3, an imaging device driver 19 which is connected to the signal line 13 and drives the CCD 11 is provided. Further, a signal processing circuit 3a is provided. In the signal processing circuit 3a, signals of a frame sequential object image picked up by the CCD 11 in a specific region, such as an R region, G1 region, G2 region, and B region, are processed. An object image can be displayed on the high resolution monitor 4 by processing imaging signals in the signal processing circuit 3a.

Figure 2:
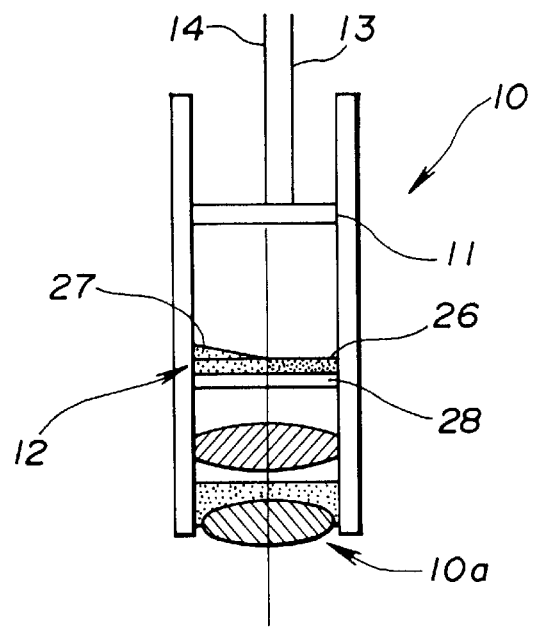
Figure 3A:
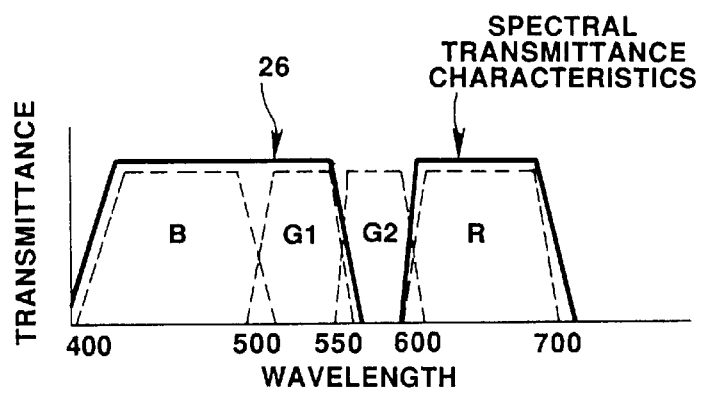
Figure 3B:
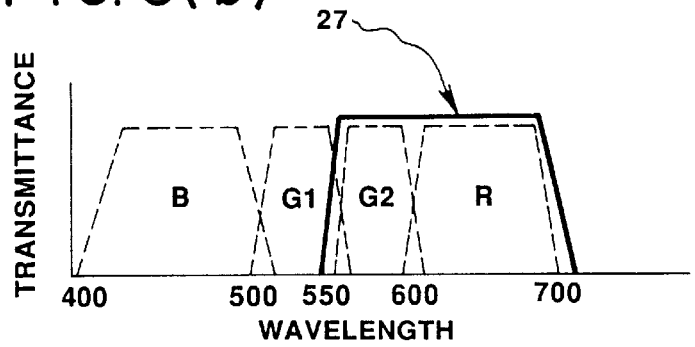

As shown in FIG. 2, the specific wavelength optical path changing means 12 is a plate glass 28 which is coated with a first transmission filter 26 and second transmission filter 27 having different transmitting characteristics, on a bisected surface facing the CCD 11. These filters transmit frame sequential reflected light from an object through the objective lens system 10a. The first transmission filter 26 transmits light, for example, light in R, G1 and B regions from among R, G1, G2 and B regions as shown in FIG. 3. The second transmission filter 27 transmits light, for example, light in R and G2 regions and shifts the optical path of the transmitted light as mentioned below.

Figure 4A:
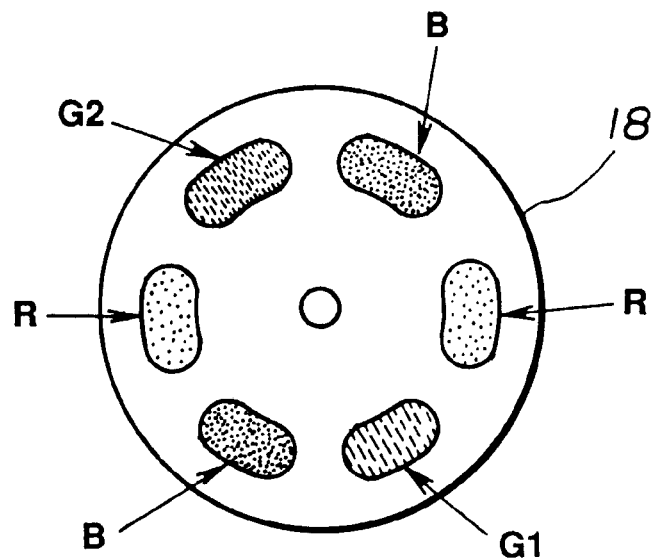
Figure 4B:
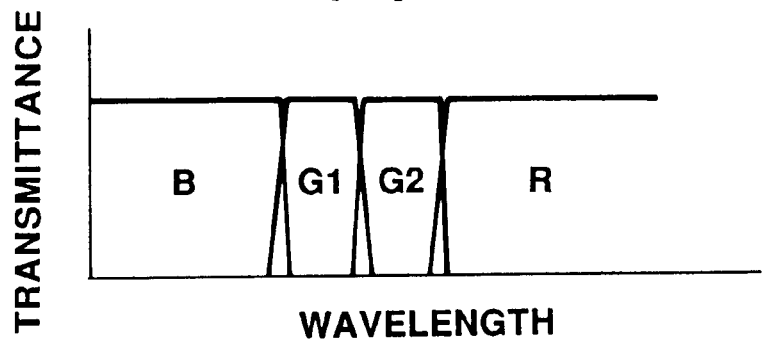

As shown in FIG. 4, in the rotary filter 18, filters for transmitting light of wavelength ranges of R, G1, G2 and B (FIG. 4(b)) are arranged in the circumference direction (FIG. 4(a)). The rotation of the motor 17 is controlled and driven by a motor driver (not illustrated).

The signal processing circuit 3a comprises an A/D converter 20 connected to the signal line 14 which A/D-convertes imaging signals originated from the CCD 11, an R frame memory 21a, G1 frame memory 21b, G2 frame memory 21c, and B frame memory 21d. These frame memories are dual-port type memory groups which store data in R region, G1 region, G2 region and B region, respectively, through a SW1 which is synchronized with the rotary filter 18 and switched to the same. The imaging signals stored in the R frame memory 21a and B frame memory 21d, and the imaging signals stored in the G1 frame memory 21b or G2 frame memory 21c through a SW2 are supplied to D/A converters 22a, 22b, and 22c. In the D/A converters, the imaging signals are D/A-converted to produce high resolution video signals. Then, an object image can be displayed on the high resolution monitor 4 through amplifiers 23a, 23b, and 23c. The provision of the A/D converter 20 is not restricted in the signal processing circuit 3a. However, the A/D converter 20 may be provided in the electronic endoscope 2.

When the amplification factor of the amplifier 23b is 1, the amplification factors of the amplifier 23a, 23b, and 23c are indicated as amplifier 23a:amplifier 23b:amplifier 23c=¼:1:½.

The reason for such a relation is that the light quantity entering the CCD 11 is different in every R region, G1 region, G2 region, and B region.

That is, when the incident light quantity entering the CCD 11 by ordinary R, G, and B illuminating light is 1, the quantity of R light becomes 1 without varying because the R light in this embodiment passes through both of the first transmission filter 26 and second transmission filter 27. The quantity of B light becomes ½ because the B light passes through only the first transmission filter 26 but do not pass though the second transmission filter 27. The quantity of G1 or G2 light becomes ½ because the G1 and G2 light have the relation to the ordinary G light as G=G1+G2. In addition, the quantity of the G1 light becomes ½ in comparison with that of the original G1 light because the G1 light passes through only the first transmission filter 26 but does not pass through the second transmission filter 27. As a result, the quantity of the G1 light entering the CCD 11 becomes ¼. Similarly, the quantity of the G2 light becomes ½ in comparison with that of the original G2 light because the G2 light passes through only the second transmission filter 27 but does not pass through the first transmission filter 26. As a result, the quantity of the G2 light entering the CCD 11 becomes ¼. These results are summarized to be the ratio of the incident light quantity of R, G1, G2, and B regions as

R:G1:G2:B=1:¼:¼:½.

In order to correct the uneven quantity of light due to this optical system, the amplification factors of the amplifiers 23a, 23b, and 23c are determined as stated above.

The unevenness of the light quantity is corrected by the amplifier 23a, 23b, and 23c. However, for example, the ratio of irradiated light quantity may be as

R:G1:G2:B=¼:1:1:½ by controlling the lamp 15, or the filter area ratio among the R region, G1 region, G2 region and B region of the rotary filter 18 may be corrected as

R:G1: G2: B=¼:1:1:½ with the constant light quantity from the lamp 15.

The signal processing circuit 3a has a memory controller 24 which controls the R frame memory 21a, G1 frame memory 21b, G2 frame memory 21c, B frame memory 21d, and SW2. The memory controller 24 generates various control clocks CLK1–CLK4 based on a reference clock CLK0 produced by a reference clock generator 25. The reference clock CLK0 is also supplied to the D/A converters 22a, 22b, and 22c. Based on the reference clock CLK0, D/A conversion is performed.

The control clock CLK1 is a control clock for reading out the R frame memory 21a and B frame memory 21d. The control clock CLK2 is a control clock for reading out the G1 frame memory 21b. The control clock CLK3 is a control clock for reading out the G2 frame memory 21c. The control clock CLK4 is a timing signal for controlling the switch of the SW2. The SW2 is switched between a side a and side b based on the control clock CLK4.

The operation of the electronic endoscope apparatus 1 serving as the frame sequential type imaging apparatus of the first embodiment formed in this manner will be explained as follows.

The light which passes through the rotary filter 18 and which is time-sequentially separated into R. G1, G2, and B wavelength ranges enters the incident end of the light guide 9. Then, the light passes through the light guide 9 and emanates from the emanating end surface 9 of the light guide 9 to illuminate an object.

Figure 6A:
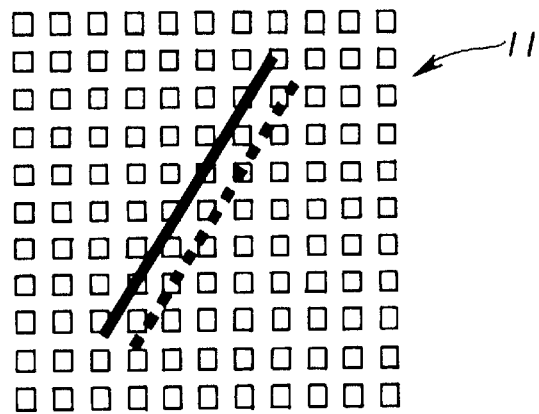

An image of the light reflected from an object irradiated by the illuminating light is formed on the CCD 11 through the objective lens system 10a and specific wavelength optical path changing means 12, and then photoelectrically converted. As shown in FIG. 6(a), for example, the R, G1 and B images of a straight line object are formed like the solid line on the imaging surface of the CCD 11 through a first transmission filter 26 by the specific wavelength optical path changing means 12. The R and G2 images passing through the second transmission filter 27 are formed in a position shifted by, for example, ½ picture element pitch in the inclined lower right direction of the R, G1 and B images like the broken line.

Since the R image passes through the first and second transmission filters 26 and 27, an image formed by rectilinear light and an image formed by the light in which the optical path is shifted are simultaneously formed on the CCD 11 (that is, double images regarding the R image are picked up). However, it is known that the space frequency components of the R image in an endoscope image are unevenly distributed in low frequency. Even if double-formed images which are shifted by about ½ picture element pitch of the CCD 11 are picked up, the resolution of an observed image is not affected.

A driving pulse from an imaging device driver 19 in the CCU 3 is applied to the CCD 11 through the signal line 13, so that readout and transmission are performed by the driving pulse. A video signal read out from the CCD 11 is supplied to an A/D converter 20 provided in the signal processing circuit 3a of the CCU 3 through the signal line 14 and converted into a digital signal. The image information which is the digital signal is selectively stored in the R frame memory 21a, G1 frame memory 21b, G2 frame memory 21c, B frame memory 21a, G1 frame memory 21b, G2 frame memory 21c and B frame memory 21d which are dual-port type memory groups in the R region, G1 region, G2 region, and B region, respectively, by means of the SW1.

Next, the readout of the imaging signals stored in the R frame memory 21a, G1 frame memory 21b, G2 frame memory 21c, and B frame memory 21d will be explained. To make the explanation simple, assuming that the CCD 11 is formed of picture elements arranged as a matrix of 3×3, the R frame memory 21a stores the R image information as shown in FIG. 7(a), G1 frame memory 21b stores the G1 image information as shown in FIG. 7(b), G2 frame memory 21c stores the G2 image information as shown in FIG. 7(c), and B frame memory 21d stores the B image information as shown in FIG. 7(d).

Figure 8:
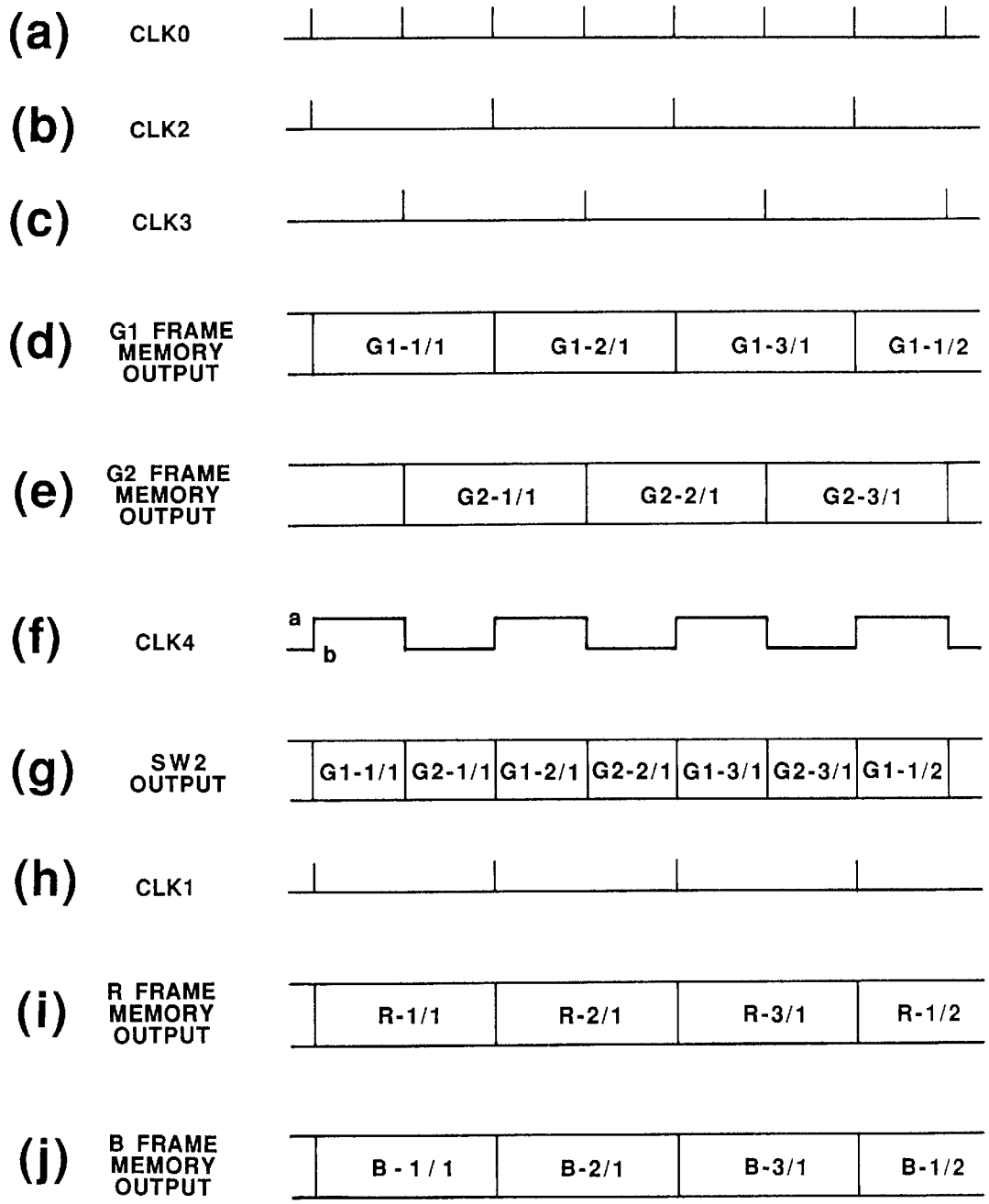

Here, when the timing of the reference clock CLK0 (see FIG. 5) is such timing as shown in FIG. 8(a), the control clock CLK2 is a clock of a double period as shown in FIG. 8(b). The control clock CLK3 is also a clock of a double period as shown in FIG. 8(c) and has a phase of 180 degrees to the control clock CLK2.

Figure 5:
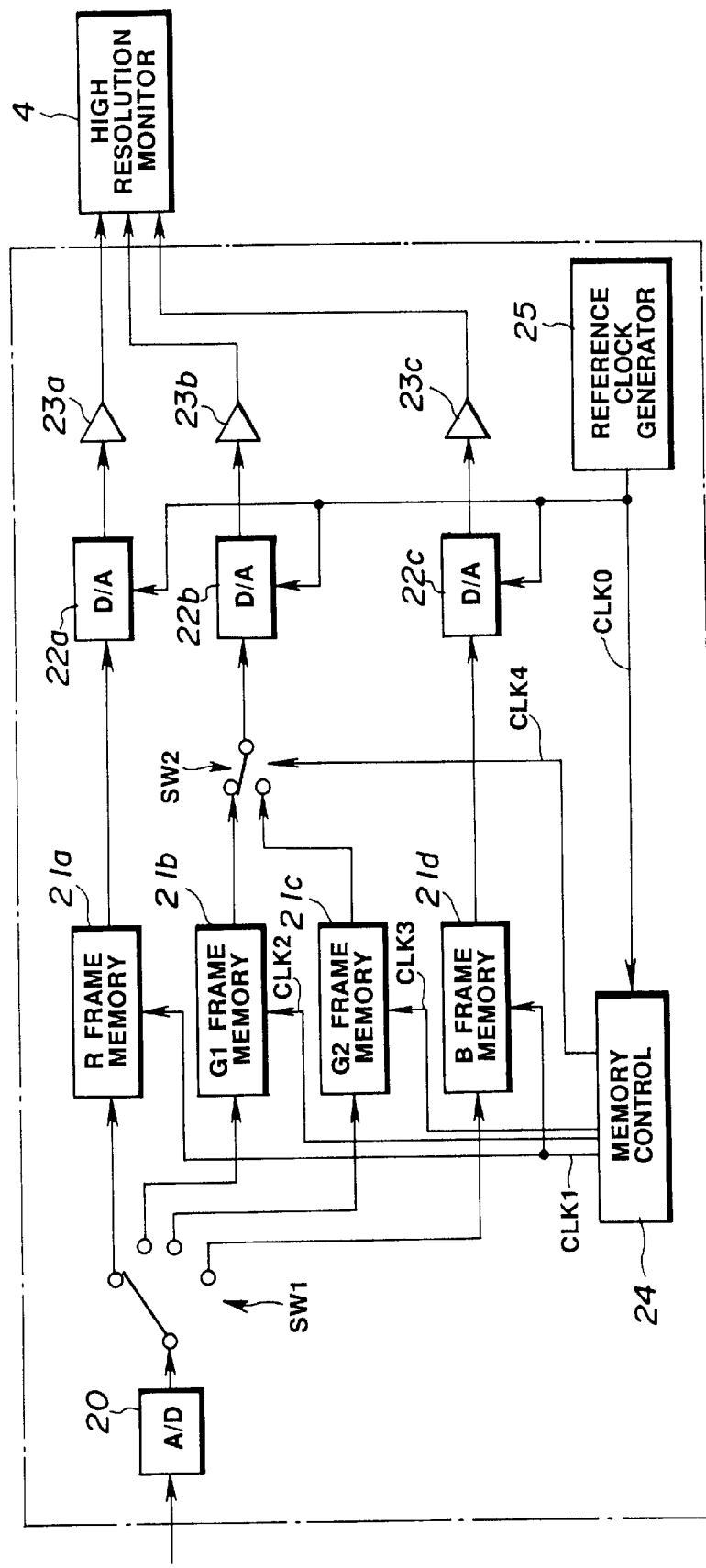

With reference to FIG. 5, the G1 image information is synchronized with the control clock CLK2 and sequentially output as G1-1/1, G1-2/1, G1-3/1, G1-1/2 . . . from the G1 frame memory 21b as shown in FIG. 8(d). Similarly, the G2 image information is synchronized with the control clock CLK3 and sequentially output as G2-1/1, G2-2/1, G2-3/1, G2-1/2 . . . from the G2 frame memory 21c as shown in FIG. 8(e).

At the same time, the control clock CLK3 controlling the switch of the SW2 is a square wave as shown in FIG. 8(f) which is synchronized with the reference clock CLK0 and reversed. When the control clock CLK3 is, for example, "H", the SW2 selects the side a and when CLK3 is "L", it selects the side b. Then, information in which the G1 image information is exchanged with the G2 image information in every reference clock CLK0 is output from the SW2. As a result, the image information of G1-1/1, G2-1/1, G1-2/1, G2-2/1, G1-3/1, G2-3/1, G1-1/2 . . . is sequentially supplied to a D/A converter 25b in every reference clock CLK0 as shown in FIG. 8(g).

Further, the control clock CLK1 is a clock of a double period as shown in FIG. 8(h) as the same as that of the control clock CLK2. The R image information is synchronized with the control clock CLK1 and sequentially output as R-1/1, R-2/1, R-3/1, R-1/2 . . . from the R frame memory 21a as shown in FIG. 8(i). Similarly, the B image information of B-1/1, B-2/1, B-3/1, B-1/2 . . . is sequentially output from the B frame memory 21d as shown in FIG. 8(j).

In this way, the R frame memory 21a and B frame memory 21d, and the G1 frame memory 21b or G2 frame memory 21c are read out through the SW2, and converted into analog signals by the D/A converters 22a, 22b, and 22c, and then, supplied to the high resolution monitor 4 through the amplifiers 23a, 23b, and 23c, so that an object is displayed in high resolution colors by the high resolution monitor 4.

Figure 9:
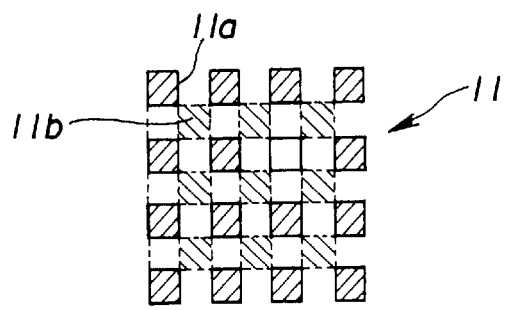

The high resolution colors are displayed as follows. Specifically, as mentioned above, the R and G2 images are formed in a position shifted by ½ picture element pitch in the inclined lower right direction of the R, G1 and B images (see FIG. 6(a)) as indicated by a broken line. Therefore, assuming that a hypothetical picture element 11b is placed in a position shifted by ½ picture element pitch in comparison with a real picture element 11a on the imaging surface of the CCD 11 as shown in FIG. 9, the R and G2 images are equal to an image formed in the hypothetical picture element 11b.

Figure 10A:
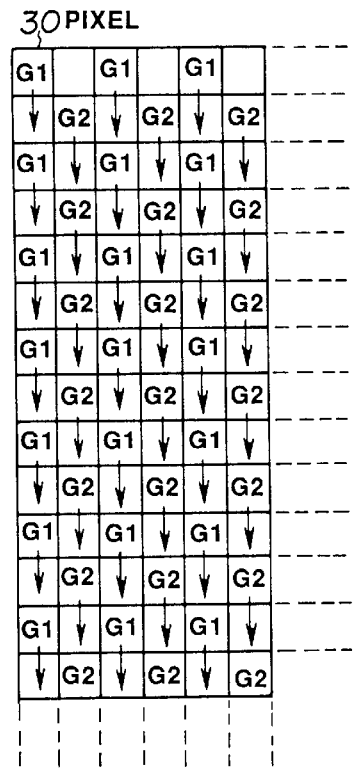

For example, if the high resolution monitor 4 is formed of pixels having double resolution in comparison with the resolution of the CCD 11, a G1 image corresponding to the real picture element 11a, a G2 image corresponding to the hypothetical picture element 11b, and an image displayed on a pixel 30 having double resolution can be obtained by copying the G1 and G2 image information of a corresponding pixel in a pixel (arrows in FIG. 10(a)) below the pixel 30 (in which RGB images are displayed) on the monitor shown in FIG. 10.

Figure 10B:
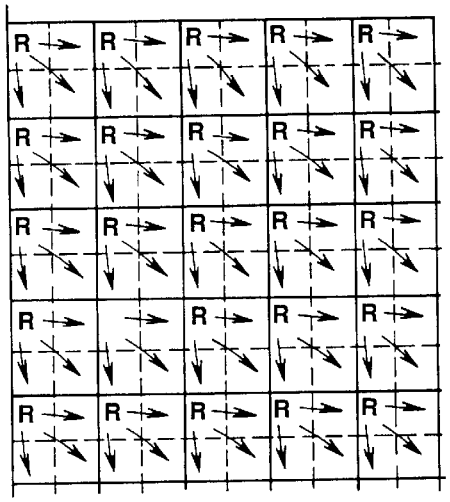
Figure 10C:
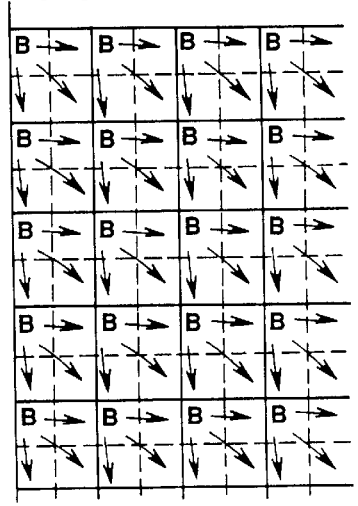

As shown in FIGS. 10(b) and 10(c), as the R and B image information, the original image information is displayed by copying the R and B images corresponding to the real picture element 11a in the right, down and lower right directions. Because the R and B images do not contribute a lot to endoscope image structure, there is no trouble that the R and B images should have such resolution as that of the G1 and G2 images.

Moreover, to copy image information, when data is written in a frame memory, a method of writing the same data in a plurality of memory addresses is used, or when data is read out, a method of maintaining original data and reading out and displaying the maintained data in accordance with a scanning address of a high resolution monitor is used.

Figure 6B:
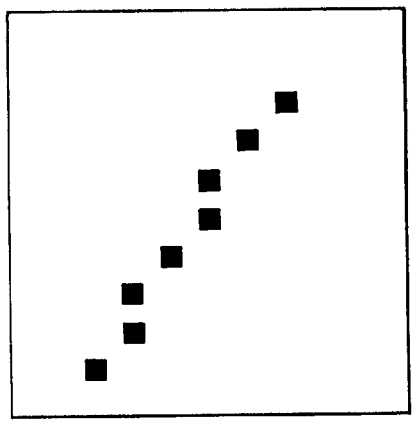
Figure 6C:
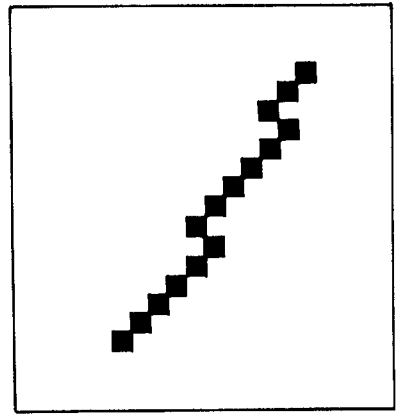

Accordingly, the electronic endoscope apparatus 1 serving as the frame sequential type imaging apparatus of the first embodiment can obtain high resolution image information by composing image information of a solid line and broken line by the specific wavelength optical path changing means 12 and SW2 as shown in FIG. 6(c) in comparison with the conventional coarse image information obtained from an image of solid lines as shown in FIG. 6(b). In addition, the electronic endoscope apparatus can display a high resolution image by performing the interpolation as shown in FIG. 10 on the high resolution monitor 4.

In this embodiment, the electronic endoscope apparatus serving as the frame sequential type imaging apparatus is explained. However, the frame sequential type imaging apparatus is not limited to the electronic endoscope apparatus and, for example, a color imaging apparatus stated in Japanese Patent Laid Open No. Hei 2-15176/1990 may be used by providing specific wavelength optical path changing means in an imaging optical system.

Although, in the spectral transmission characteristics of the first and second transmission filters 26 and 27, both filters transmit R component to effectively use incident light, the characteristic of the second filter 27 may transmit only a G2 component if it is allowable to sacrifice sensitivity. In this manner, the aforesaid R image becomes double can be avoided.

Figure 11A:
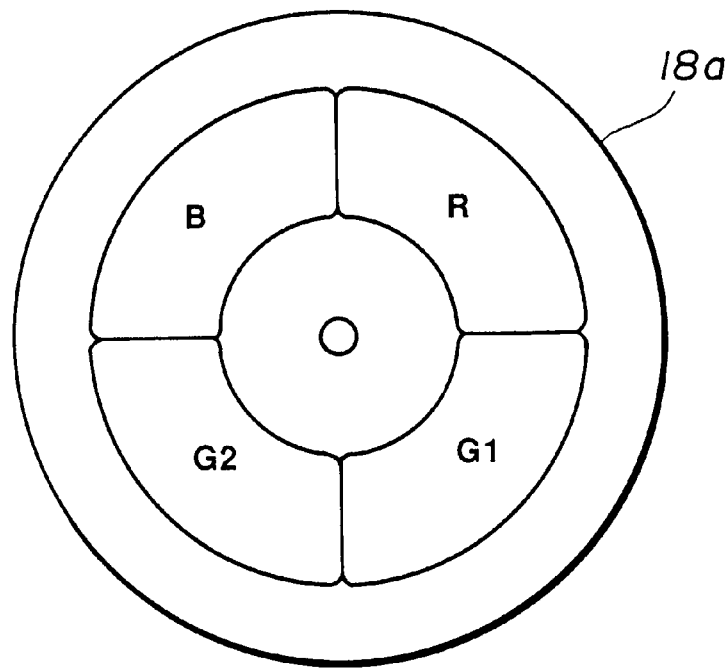
Figure 11B:
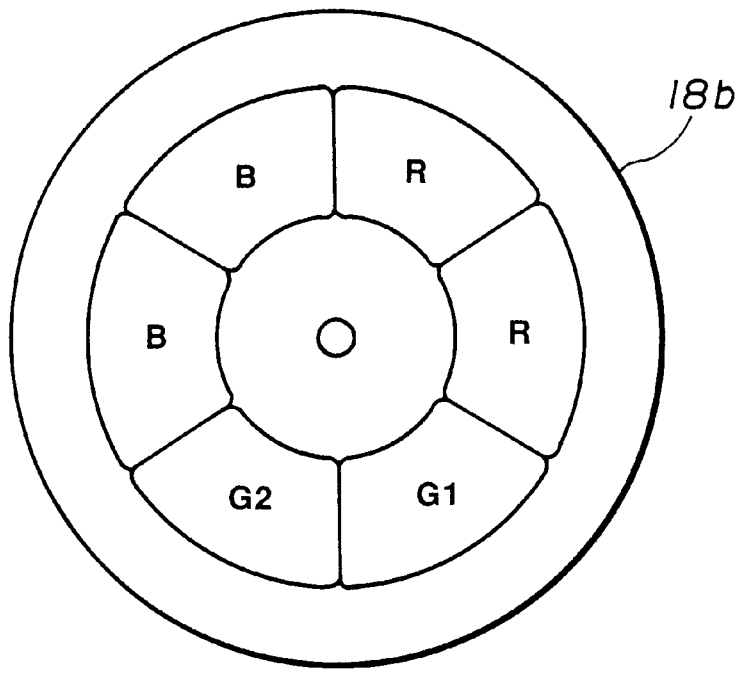

Further, a rotary filter may be formed as shown in FIG. 11(a) or 11(b). The G light is divided into two regions and emitted; however, it may be divided into more than two regions and emitted.

Next, the second embodiment will be explained. Since the second embodiment is different from the first embodiment only in the construction of the specific wavelength optical path changing means, only different construction will be explained and the explanation of the same construction will be omitted.

Figures 12A, 12B:
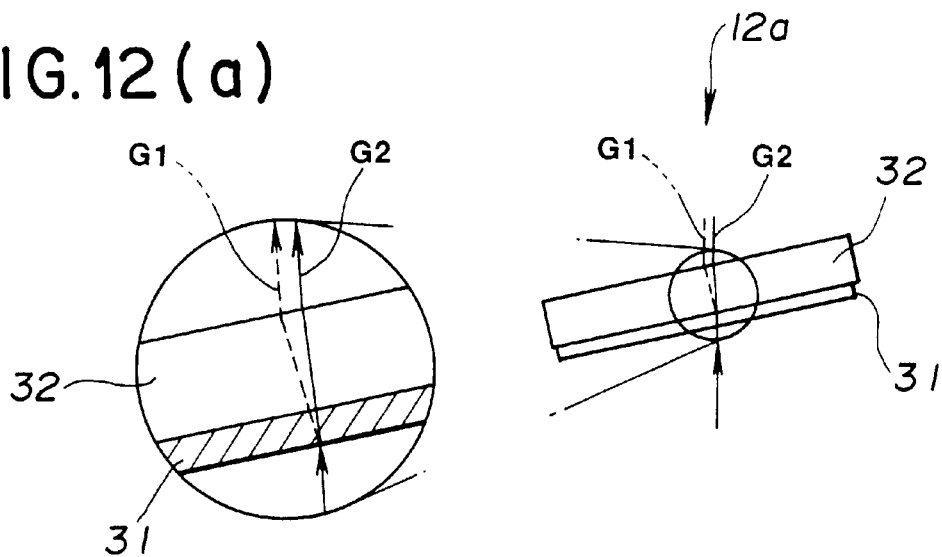
FIG. 12 is a diagram showing construction of specific wavelength optical path changing means related to the second embodiment.

As shown in FIG. 12, specific wavelength optical path changing means 12a of the second embodiment is formed of a plate glass 32 where an incident surface is coated with a wavelength selective coating film 31, and arranged to be inclined to an incident optical path.

The other construction is the same as that of the first embodiment.

In the specific wavelength optical path changing means 12a formed in this way, a small quantity of G1 light emanates from the plate glass 32 after the optical path of the G1 light is moved in parallel with the original optical path. At the same time, G2 light emanates from the plate glass 32 after the optical path of the G2 light is moved more than the movement of the G1 light. As a result, an image forming positions by means of the G1 and G2 light can be shifted.

When the R and B images are shifted one pitch or more, these images may be electrically shifted in the direction of the original positions. Assuming that the R and B regions are used to determine colors, there is no practical trouble even if the R and B components are spectrally separated by a prism or plate glass so that an image is out of focus.

The other operation and effects are the same as those of the first embodiment.

Next, the third embodiment will be explained. The third embodiment is different from the first embodiment only in the construction of an imaging optical system. Therefore, only a different construction will be explained and the explanation of the same structure will be omitted.

Figure 13:
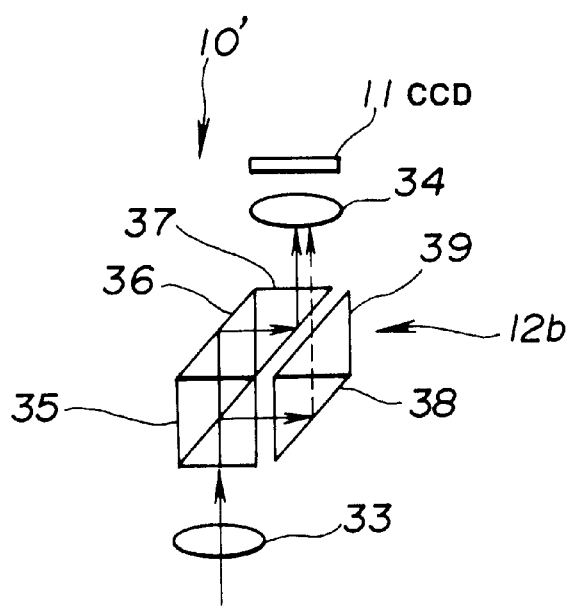
FIG. 13 is a diagram showing construction of an imaging optical system related to the third embodiment.

As shown in FIG. 13, an imaging optical system 10' comprises an image picking up lens 33 which converts reflected light emitted from an object into parallel light, specific wavelength optical path changing means 12b which shifts an optical path of light in a G2 wavelength range of the parallel light emitted from the image picking up lens 33, and an image forming lens 34 which makes light through the specific wavelength optical path changing means 12b form an image on an imaging surface of a CCD 11.

In the specific wavelength optical path changing means 12b, a dichroic mirror 35 reflects only G2 image light and makes G1, R, and B image light of the parallel light travel straight by the image picking up lens 33. Then, the G2 image light enters an image forming lens 34 in a state in which the optical path of the G2 image light is shifted from the optical paths of the G1, R, and B image light travelling straight and forms an image on the CCD 11 by means of prisms 38 and 39.

The other construction, operation, and effects are the same as those of the first embodiment.

Next, the fourth embodiment will be explained. The fourth embodiment is different from the first embodiment only in the construction of specific wavelength optical path changing means. Therefore, only different construction will be explained and the explanation of the same construction will be omitted.

Figure 14:
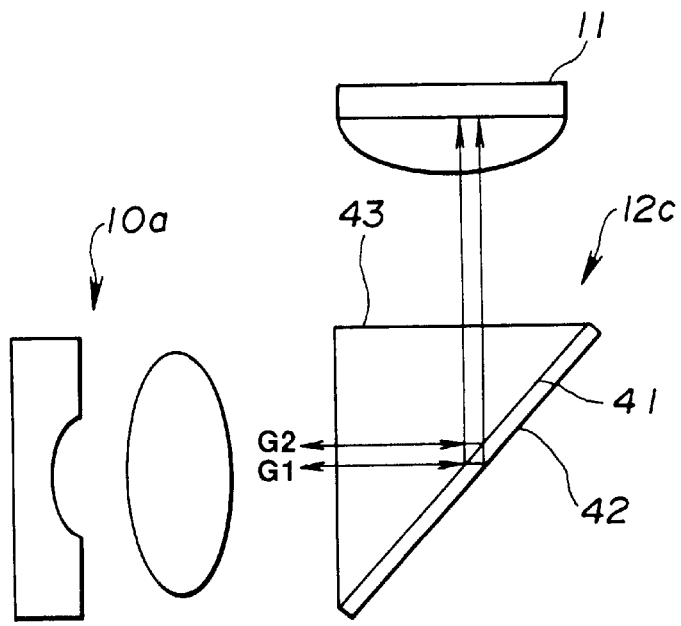
FIGS. 14 to 17 relate to the fourth embodiment.
Figure 15A:
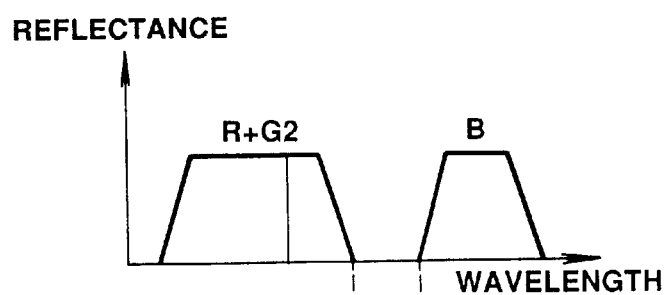
Figure 15B:
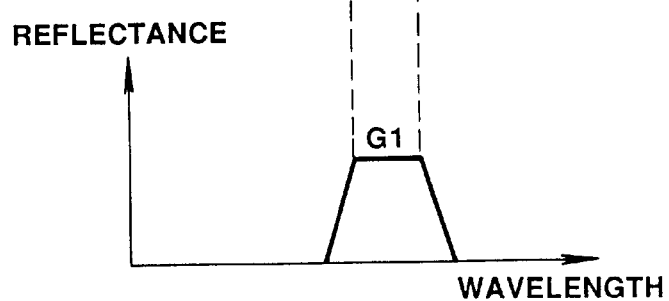

As shown in FIG. 14, specific wavelength optical path changing means 12c is a prism 43 having a reflecting surface 41 reflecting R, G2, and B components from among object images through an objective lens system 10a and a reflecting surface 42 reflecting G1 components. Reflectance characteristics of the reflecting surfaces 41 and 42 are shown in FIG. 15 (FIG. 15(a) is the reflectance characteristics of the reflecting surface 41 and FIG. 15(b) is the reflecting surface 42). The reflecting surfaces 41 and 42 are formed of a metallic evaporation film or the like. The distance between the reflecting surfaces 41 and 42 is the length in which image forming positions of the G1 image and G2 image on the CCD 11 are shifted by ½ picture element pitch.

Figure 16:
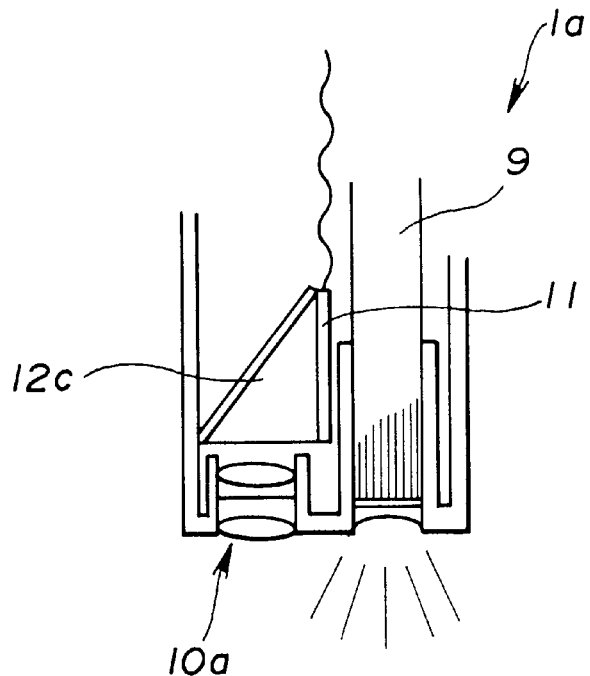
Figure 17:
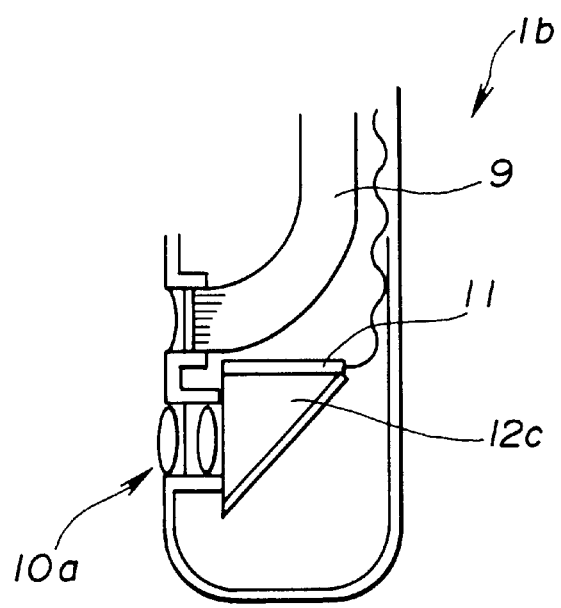

Such specific wavelength optical path changing means is used in a forward-viewing type electronic endoscope apparatus 1a having a tip portion as shown in FIG. 16 and in a side-viewing type electronic endoscope apparatus 1b having a tip portion as shown in FIG. 17.

The other construction, operation, and effects are the same as those of the first embodiment.

Next, the fifth embodiment will be explained. Since the fifth embodiment is different from the first embodiment only in the construction of specific wavelength optical path changing means, only different construction will be explained and the explanation of the same construction will be omitted.

Figure 18A:
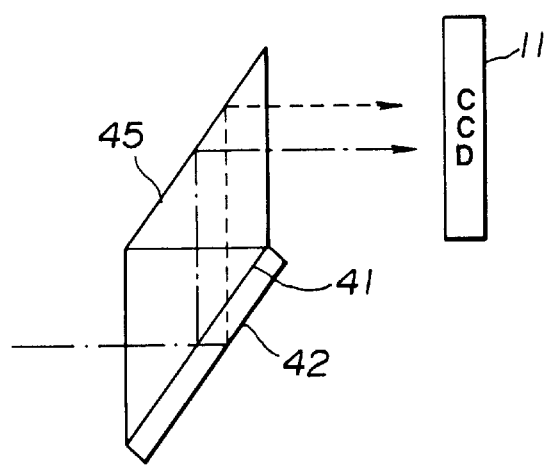
FIG. 18 is a diagram showing construction of specific wavelength optical path changing means related to the fifth embodiment.
Figure 18B:
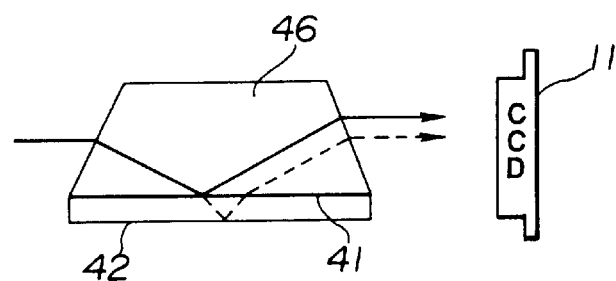

In the fifth embodiment, specific wavelength optical path changing means is formed of one or two prisms. That is, as a first concrete example, a reflecting surface 41 for reflecting R, G2, and B components and a reflecting surface 42 for reflecting a G1 component are provided on one surface of a parallelogram prism 45 by means of a metallic evaporation film or the like as shown in FIG. 18(a). As a second concrete example, a reflecting surface 41 for reflecting R, G2 and B components and a reflecting surface 42 for reflecting R, G2 and B components are provided on the base of a trapezoid prism 46 by means of a metallic evaporation film or the like as shown in FIG. 18(b). G1 image and G2 image are shifted and formed on a CCD 11 using these reflecting surfaces 41 and 42.

Figure 18C:
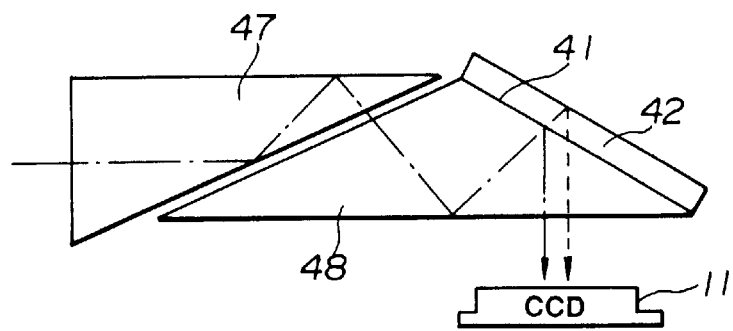

The reflectance characteristics of the reflecting surfaces 41 and 42 are made in the same way as that of the fourth embodiment. As shown in FIG. 18(c), the specific wavelength optical path changing means may be formed of two triangle prisms 47 and 48.

The other construction, operation, and effects are the same as those of the first embodiment.

Next, the sixth embodiment will be explained. In the sixth embodiment, a high resolution image can be obtained by shifting B and G images while an image is obtained by separating the G1 and G2 wavelength light in the first to fifth embodiments. That is, in the sixth embodiment, the construction of a rotary filter 18 is different from that of the first embodiment and spectral transmission characteristics of a first transmission filter 26 and second transmission filter 27 are different from those of the first embodiment. Further, the sixth embodiment is equal to the first embodiment except that the construction of a signal processing circuit for processing image signals and performing interpolation of image information on a high resolution monitor 4 is different. Thus, only different construction will be explained and the explanation of the same construction will be omitted.

Figure 19A:
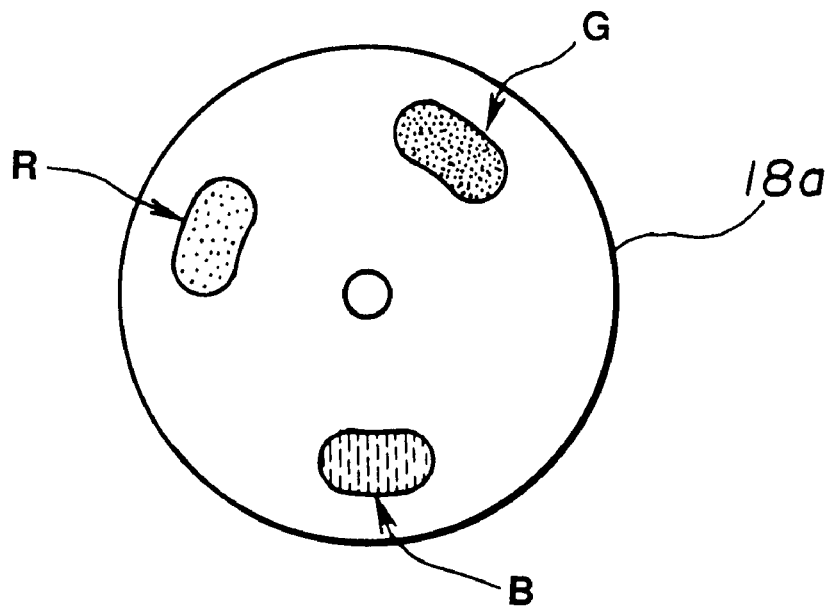
Figure 19B:
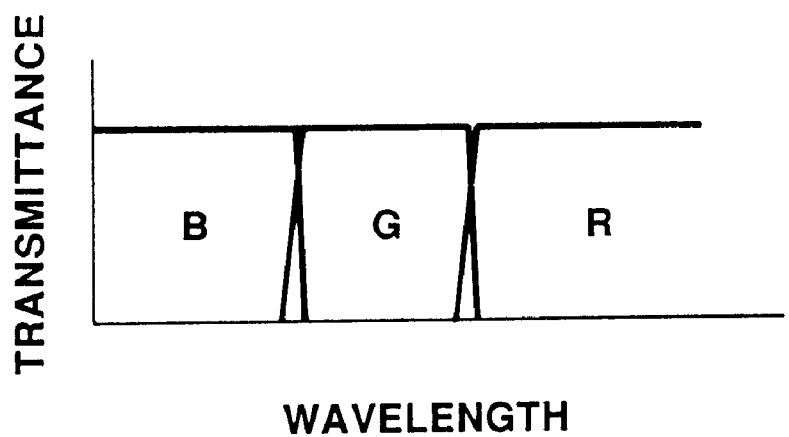

As shown in FIG. 19, in a rotary filter 18a of the sixth embodiment, filters for transmitting light of R, G and B wavelength ranges (FIG. 19(b)) are arranged in the circumference direction (FIG. 19(a)).

In the sixth embodiment, as the spectral transmission characteristics of the first transmission filter 26 and second transmission filter 27, the first transmission filter 26 transmits R and G components and the second transmission filter transmits a B component.

A signal processing circuit 3b of the sixth embodiment comprises, for example, a R frame memory 21a, G frame memory 21e, and B frame memory 21d, which are dual-port type memory groups memorizing the image information from an A/D converter 20 through a SW1 being able to synchronize the image information with the aforesaid rotary filter 18a and switch the information to the filter 18a. Then, the picture information stored in the R frame memory 21a is supplied to a D/A converter 22a. The image information stored in the G frame memory 21e and B frame memory 21d is supplied to a D/A converters 22b and 22c through buffers 49a and 49b, respectively. The image information is D/A-converted by the D/A converters 22a, 22b, and 22c to produce a high resolution video signal. Then, an object image is displayed on a high resolution monitor 4 through amplifiers 23a, 23b, and 23c.

A memory controller 24 of the signal processing circuit 3b generates various control clocks CLK1 and CLK2 based on a reference clock CLK0 produced by a reference clock generator 25. The reference clock CLK0 is also supplied to the D/A converters 22a, 22b, and 22c, so that these converters D/A-convert the image information based on the reference clock CLK0.

The control clock CLK1 is a control clock for reading out the R frame memory 21a, G frame memory 21e, and B frame memory 21d. The control clock CLK2 is a control clock for controlling the buffers 49a and 49b. The control clock CLK2 is inverted by an inverter 49c and supplied to the buffer 49b. The buffer 49a outputs G image information stored in the G frame memory 21e when the control clock CLK2 is "H". At the same time, since the buffer 49b receives the control clock CLK2 through the inverter 49c, the buffer 49b outputs the B image information stored in the B frame memory 21d when the control clock CLK2 is "L".

The other construction is the same as that of the first embodiment.

Figure 21A:
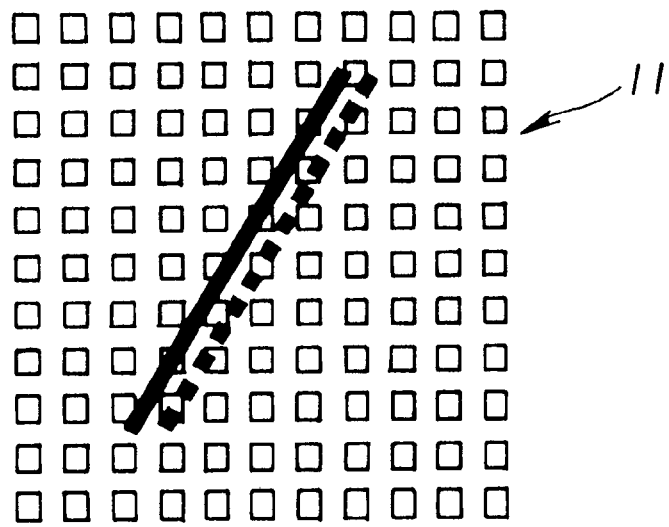

In the frame sequential type imaging apparatus of the sixth embodiment formed in this way, a B image is formed (shown by a broken line) in a position shifted from the R and G images of a solid line on the CCD 11 as shown in FIG. 21(a). The readout of the imaging signal stored in the R frame memory 21a, G frame memory 21e, and B frame memory 21d in which image information of each formed image is stored will be explained. Therefore, to make the explanation simple, assuming that the CCD 11 is formed of picture elements arranged in a 3×3 matrix, the R frame memory 21a at this time stores the R image information as shown in FIG. 22(a), the G frame memory 21e stores the G image information as shown in FIG. 22(b), and the B frame memory 21d stores the B image information as shown in FIG. 22(c).

When the timing of the reference clock CLK0 is the timing shown in FIG. 23(a), the control clock CLK1 is a double period clock as shown in FIG. 23(b). The control clock CLK2 is a square wave which is synchronized with the reference clock CLK0 and inverted as shown in FIG. 23(c).

Figure 20:
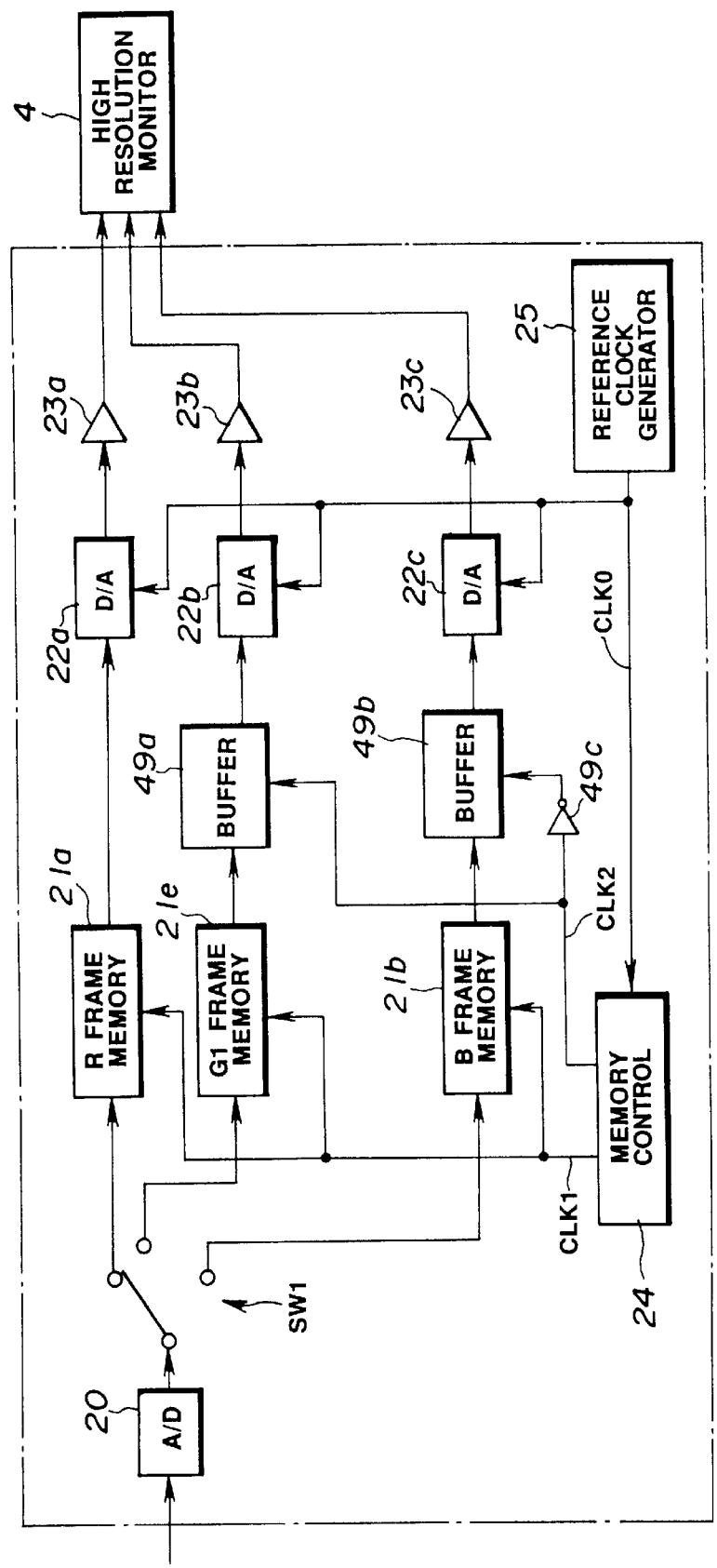

In reference to FIG. 20, the R image information is synchronized with the control clock CLK1 and sequentially supplied from the R frame memory 21a as R-1/1, R-2/1, R-3/1, R-1/2 . . . to the D/A converter 22a as shown in FIG. 23(d).

At the same time, when the control clock CLK2 is "H", the buffer 49a is active and intermittently supplies output of G-1/1, G-2/1, G-3/1, G-1/2 . . . as shown in FIG. 23(e) to the D/A converter 22c. When the control clock CLK2 is "L", the buffer 49b is active and intermittently supplies output of G-1/1, G-2/1, G-3/1, G-1/2 . . . as shown in FIG. 23(f) to a D/A converter 22c. That is, the image information is alternately supplied to the D/A converters 22b and 22c.

Figure 21B:
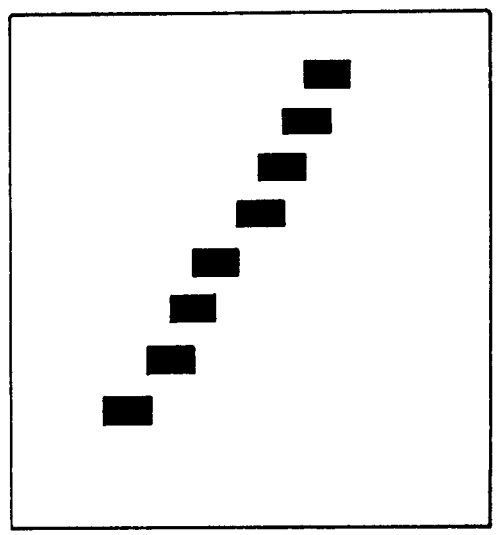

The image information is read out in this way, so that the R and G images of solid lines and the B image of a broken line are synthesized and that the high resolution picture image can be obtained as shown in FIG. 21(b).

Figure 24:
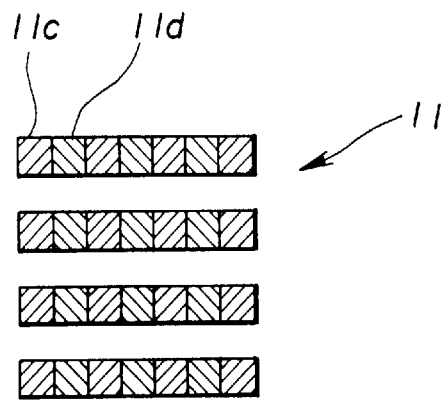

The B image is formed as the broken line in a position shifted by ½ picture element pitch from the R and G images in the right direction (FIG. 21(a)). Therefore, as shown in FIG. 24, assuming that a hypothetical picture element lid is located in a position shifted by ½ picture element pitch from a real picture element 11c on the imaging surface of the CCD 11, the B image is equal to the image formed in the hypothetical picture element 11d.

Figure 25A:
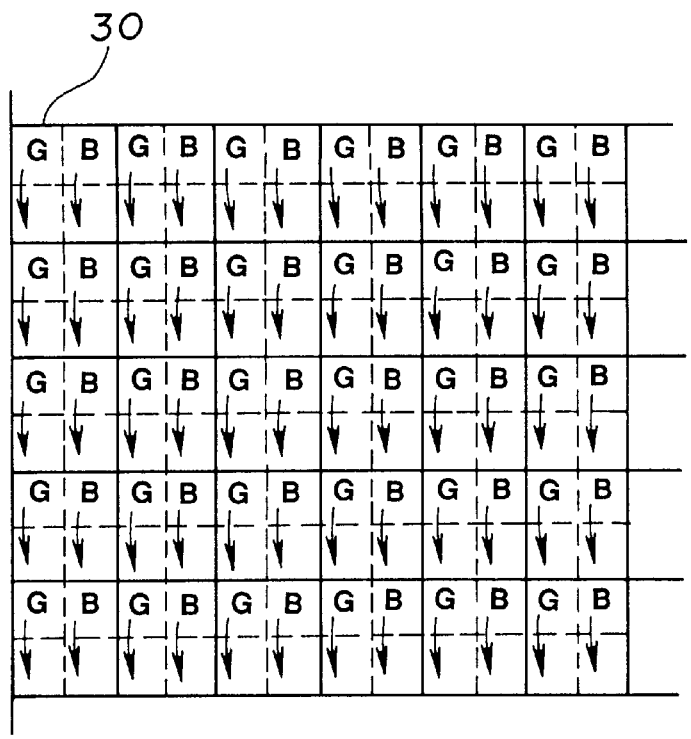

For example, if the high resolution monitor 4 is formed of pixels having double resolution in comparison with the resolution of the CCD 11, the R image corresponding to the real picture element 11c, the G image corresponding to the hypothetical picture element 11d, and an image which is displayed in pixels 30 and which has double resolution can be obtained by copying the R and G image information of a corresponding pixel in one pixel below the pixel (arrows in FIG. 25(A)) in the pixels 30 (R, G and B images are displayed in one of the pixels 30) on a monitor shown in FIG. 25.

Figure 25B:
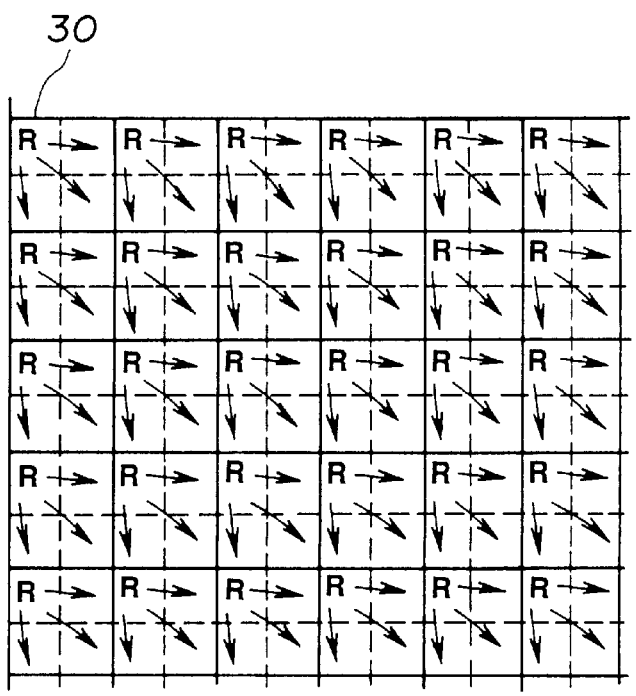

As the B image information, original image information is displayed by copying the R image corresponding to the real picture element 11a in the directions of right, down and lower right as shown in FIG. 25(b).

The other operation is the same as that of the first embodiment.

In this manner, the R, G, and B illuminating light currently in use can be used in the frame sequential type imaging apparatus of the sixth embodiment and high resolution image information can be obtained by forming simple construction.

Next, the seventh embodiment will be explained. The seventh embodiment is different from the first embodiment only in the construction of specific wavelength optical path changing means and the construction of an objective lens system using an anamorphic lens. Thus, only different construction will be explained and the explanation of the same construction will be omitted.

The CCD for endoscope currently in use is a square shape or a shape in which the ratio of length to width is three to four corresponding to the aspect ratio of the present television standard. However, the CCD for high vision is a shape in which the ratio of the length to width is three to five. When a full image is displayed on a TV monitor, a CCD having longer sideways should be used. If such a CCD having longer sideways is used, the outer diameter of the tip of an endoscope becomes wider. Then, the seventh embodiment provides a frame sequential type imaging apparatus applicable to a high vision TV.

Figure 26:
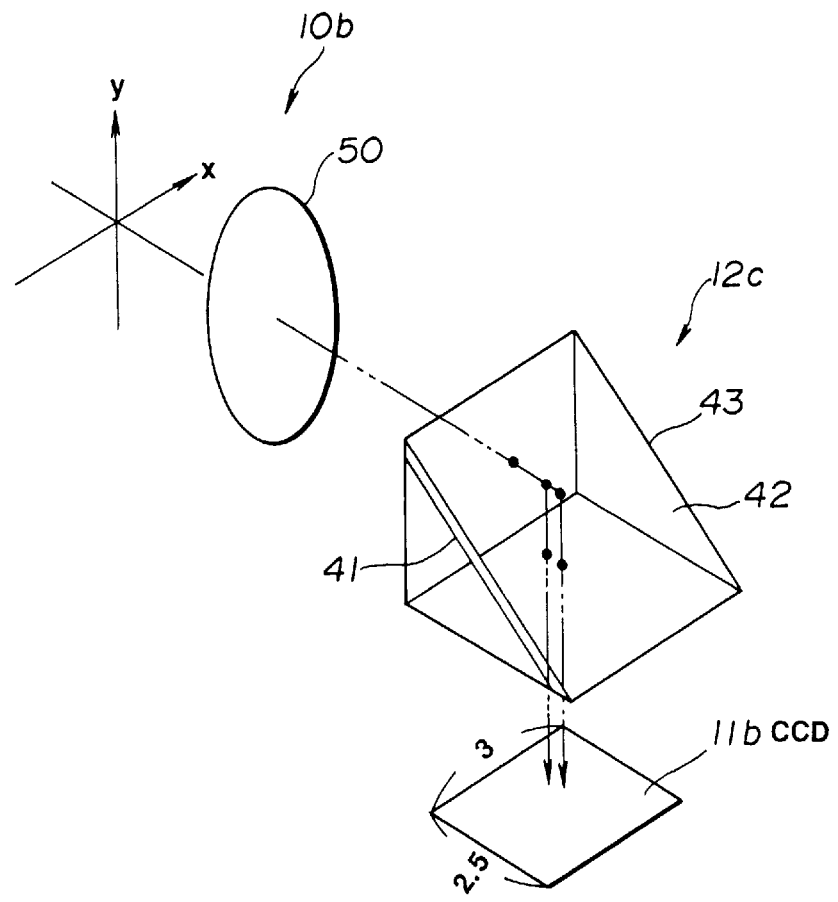
FIGS. 26 to 28 relate to the seventh embodiment.

As shown in FIG. 26, an imaging optical system of a frame sequential type imaging apparatus of the seventh embodiment comprises an objective lens system 10b using an anamorphic lens 50 having different magnifying powers in the x and y directions on x–y coordinates on a surface lying at right angles to the optical axis of the reflected light, specific wavelength optical path changing means 12c, and a CCD 11a in which the ratio of the length to width is three to 2.5. The specific wavelength optical path changing means 12c is similar to that of the fourth embodiment, that is, the specific wavelength optical path changing means 12c is a prism 43 having a reflecting surface 41 which reflects R, G2, and B components of an object image through the object lens system 10b and a reflecting surface 42 which reflects a G1 component. The reflectance characteristics of the reflecting surfaces 41 and 42 are shown in FIG. 11 (FIG. 15(a) is the reflecting characteristics of the reflecting surface 41 and FIG. 15(b) is the reflecting characteristics of the reflecting surface 42). These reflecting surfaces 41 and 42 are made of a metallic evaporation film or the like. The distance between the reflecting surfaces 41 and 42 is the length in which an image forming position of the G1 image is shifted by ½ picture element pitch from that of the G2 image on the CCD 11.

The imaging optical system of such a frame sequential type imaging apparatus can be used for, for example, a forward-viewing type electronic endoscope apparatus 1a having a tip portion shown in FIG. 16 and a side-viewing type electronic endoscope apparatus 1b having a tip portion shown in FIG. 17.

Figure 27A:
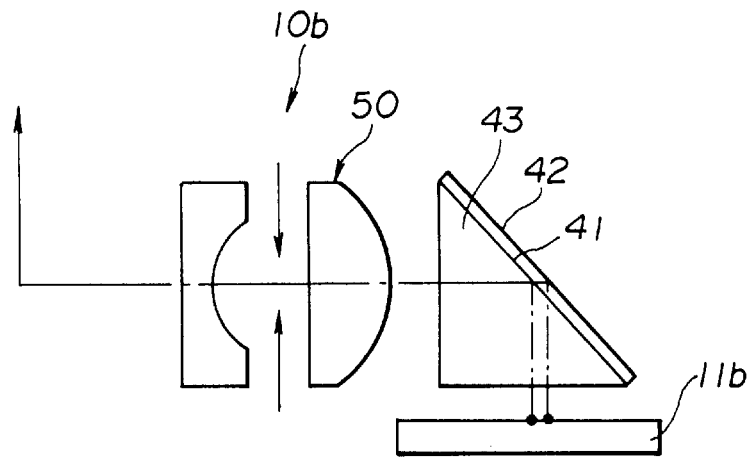
Figure 27B:
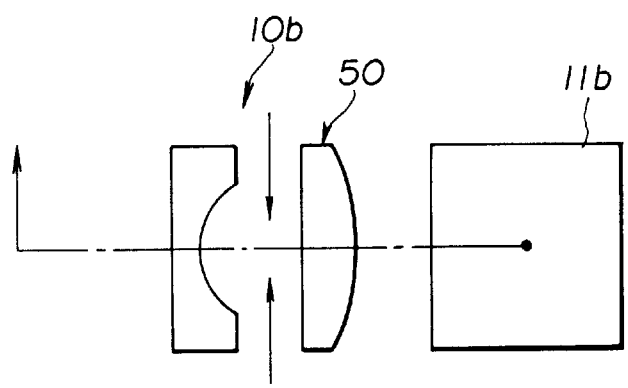
Figure 28:
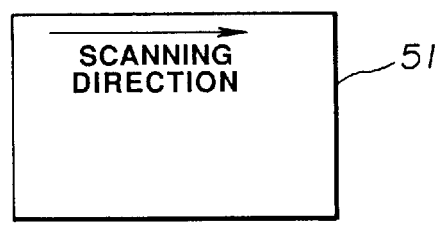

As shown in FIG. 27, the anamorphic lens 50 has a magnifying power in the y axis direction which is ½ of that in the x axis direction. Assuming that the magnifying power in the x axis is one, the magnifying power is the y axis direction is ½(FIG. 27(a) is a section in the y direction and FIG. 27(b) is a section in the x direction).

Accordingly, for example, an object which has the height of five in the y direction is imaged to be 2.5 on the CCD 11b and an object which has the height of three in the X direction is imaged to be three on the CCD 11b. The resolution in the y direction is double of that in the x direction by means of a color shifting method using the prism 43. Therefore, the y-axis component of an imaging signal obtained by the CCD 11b is electrically processed and the scanning side in the y direction is enlarged to be double, so that an image having the aspect ratio of three to five can be obtained without lowering the resolution. The electrical processing of the y-axis component of the imaging signal obtained by the CCD 11b divides the reference clock CLK0 of the first embodiment, produces a double period clock CLK0' in comparison with the reference clock CLK0, and generates control clocks CLK1'-4' in a memory control 24. These control clocks CLK1'-4' become double period clocks in comparison with the control clocks CLK1-4. Accordingly, image information is read out by the control clocks CLK1'-4', so that the image information can be electrically enlarged in the horizontal direction (y direction).

Also, it is desirable that colors are shifted in the scanning direction (lengthwise direction) of a real high vision monitor 51.

Thus, in the seventh embodiment, the quantity of information which can display a full picture plane on a high vision monitor using a CCD of approximately a square shape can be obtained. Therefore, for example, the CCD is used in an endoscope having a tip of narrow-diameter or the like, so that imaging signals for high vision with high resolution can be obtained.

Next, the eighth embodiment will be explained. In the eighth embodiment, the frame sequential type imaging apparatus of this invention is applied to a microscope apparatus.

Figure 29:
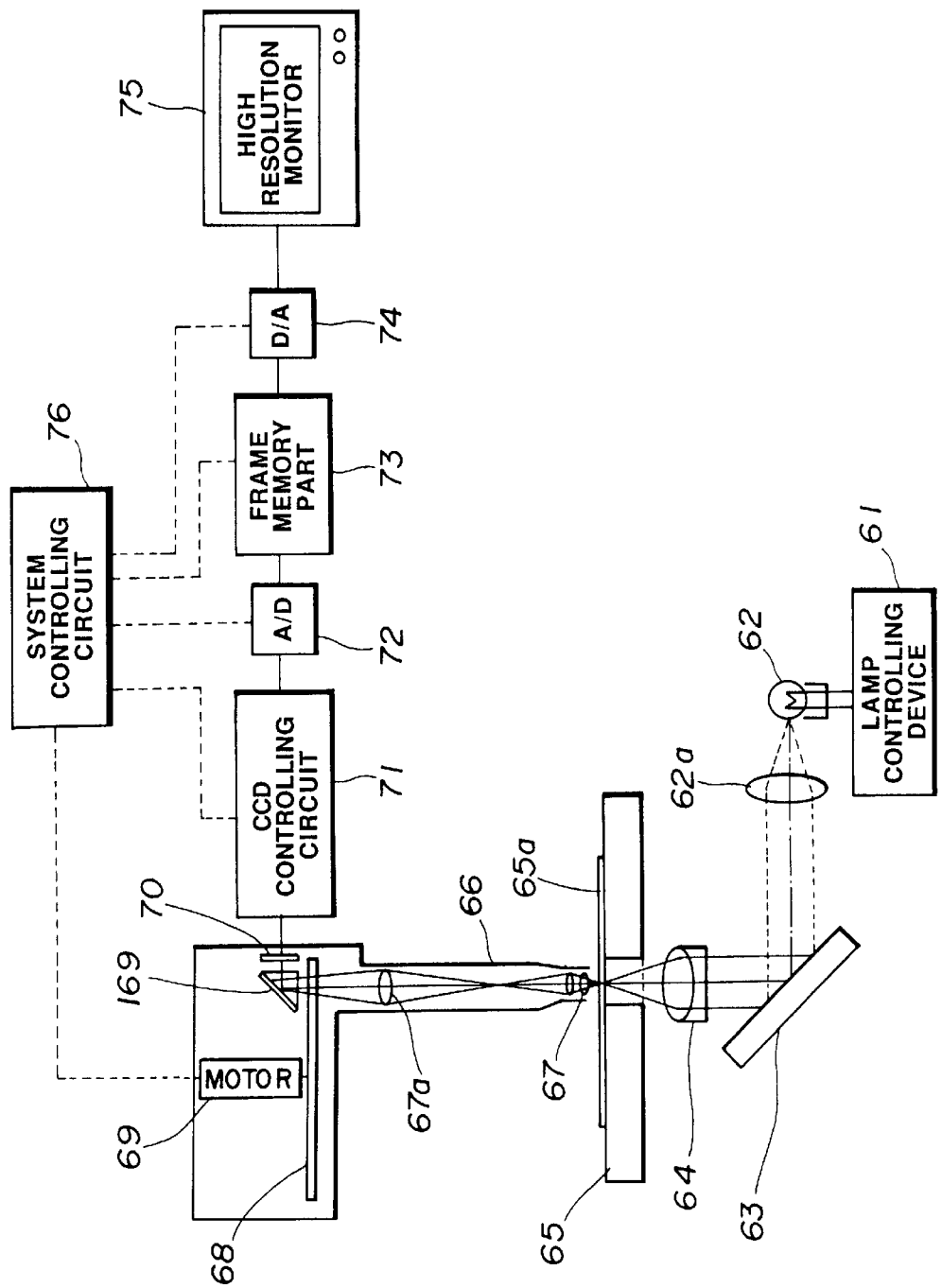
FIG. 29 is a diagram showing construction of a microscope apparatus serving as a frame sequential type imaging apparatus related to the eighth embodiment.

As shown in FIG. 29, the microscope apparatus of this embodiment converts light originated from a lamp 62 driven and controlled by a lamp controlling device 61 into approximately parallel light by a condenser lens 62a. An optical path of the parallel light is curved into 90 degrees by a reflecting mirror 63 and the parallel light is converged on an observed object arranged on a slide glass 65a on a stage 65 by a condenser lens 64. The light passing through an observed object enters a rotary filter 68 through an objective lens 67 provided in the tip portion of the microscope barrel 66 and an image forming lens 67a in the proximal end. The rotary filter 68 is rotated by a motor 69. The construction of the rotary filter 68 is the same as that of the rotary filter 18 (see FIG. 4) of the first embodiment. The rotary filter 68 converts the light which has passed through an observed object into frame sequential light of a plurality of wavelength ranges in accordance with the transmission characteristics of the observed object. An optical axis of the frame sequential light in a predetermined specific wavelength range is shifted by specific wavelength optical path changing means 169 having the same construction as that of the specific wavelength optical path changing means 12b explained in the fourth embodiment and an image is formed on an imaging surface of a CCD 70 in accordance with the transmission characteristics of the observed object. A predetermined specific wavelength range of the frame sequential light is shifted by specific wavelength optical path changing means 169 having the same construction as that of the specific wavelength optical path changing means 12b explained in the fourth embodiment and an image is formed on an imaging surface of the CCD 70.

The CCD 70 is driven by a CCD controlling circuit 71. An imaging signal supplied from the CCD 70 is preliminary processed by the CCD controlling circuit 71 and fed to an A/D converter 72 as a video signal. The video signal becoming a digital signal by the A/D converter 72 is transmitted to a frame memory portion 73 composed of frame memories of wavelength ranges, and stored as image information. The information stored in the frame memory portion 73 is simultaneously read out and sent to a high resolution monitor 75 through a D/A converter 74. Thus, a microscope image of an observed object can be observed with high resolution.

The motor 69, CCD controlling circuit 71, and A/D converter 72 are driven and controlled by synchronized various controlling signals supplied from a system controlling circuit 76. The system controlling circuit 76 generates a control clock in the same manner as that of the memory control 24 of the first embodiment and controls the reading out of the frame memory portion 73 and D/A converter 74. Detailed control of this embodiment is the same as that of the first embodiment. Thus, the explanation will be omitted.

According to the microscope apparatus as the frame sequential type imaging apparatus of the present embodiment formed in this way, a high resolution image can be displayed on the high resolution monitor 75 in the same manner as that of the first embodiment.

In this invention, it is apparent that working modes different in a wide range can be formed on the basis of the invention without departing from the spirit and scope of the invention. This invention is not restricted by its specific working mode except that it is limited by the appended claims.

What is claimed is:

1. A frame sequential type imaging apparatus comprising:

irradiating means for irradiating light on an object;

image pick-up means for sequentially picking up an observed image of said object in three or more of a plurality of wavelength ranges by the light emitted by said irradiating means; and image forming position changing means for forming an observed image picked up by said image pick-up means in at least two wavelength ranges in a same position of said plurality of wavelength ranges on an imaging surface of said image picking up means and forming an observed image in at least one of the remaining of said plurality of wavelength ranges in an offset position different from said same position, wherein said offset position produced by said image forming position changing means is a function of the wavelength range of the light emitted by said irradiating means and wherein said image forming position changing means includes a single set of optical elements which are nonmovingly fixed in position such that all of said plurality of wavelength ranges pass through said single set of optical elements.

2. The frame sequential type imaging apparatus according to claim 1, wherein said offset position different from said same position is a position shifted a predetermined amount from said same position.

3. The frame sequential type imaging apparatus according to claim 1, wherein said predetermined amount is ½ picture element pitch of said image pick-up means.

4. The frame sequential type imaging apparatus according to any one of claims 1–3, wherein said observed image picked up by said image pick-up means is an observed image irradiated by reflected light from said object, said reflected light being emitted by said irradiating means, further comprising:

wavelength range separating means for separating the light emitted by said irradiating means into light in said plurality of wavelength ranges and irradiating the light on said object.

5. The frame sequential type imaging apparatus according to claim 4, wherein said wavelength range separating means separates light in a specific wavelength range into multiple light, and said image forming position changing means forms an observed image irradiated by light in at least a part of said specific wavelength range separated by said wavelength range separating means in said offset position different from said same position.

6. The frame sequential type imaging apparatus according to claim 5, wherein light of said plurality of wavelength ranges is an R light, G light, and B light and light of said specific wavelength range is a G light.

7. The frame sequential type imaging apparatus according to claim 5, further comprising:

memorizing means for memorizing said observed image picked up by said image pick-up means as image information in each of said plurality of wavelength ranges; and signal processing means for processing signals of image information of said observed image memorized by said memorizing means.

8. The frame sequential type imaging apparatus according to claim 5, wherein said image forming position changing means includes three or more of a plurality of filters transmitting said reflected light and having different wavelength transmission characteristics, and said image forming position changing means forms said observed image having passed through at least two of said plurality of filters in said same position and forms said observed image having passed through at least one of remainder of said plurality of filters in said offset position different from said same position.

9. The frame sequential type imaging apparatus according to claim 5, wherein said image forming position changing means is a prism reflecting said reflected light and including a plurality of reflecting surfaces having different reflecting characteristics depending on wavelength ranges.

10. The frame sequential type imaging apparatus according to claim 6, further comprising, for an observed image formed in said image pick-up means in one direction on rectangular coordinates on a surface lying at right angles to an optical axis of said reflected light, image transforming means for extending and compressing said observed image in a direction lying at right angles to said one direction to transform said observed image.

11. The frame sequential type imaging apparatus according to claim 10, further comprising:

memorizing means for memorizing said observed image picked up by said image pick-up means and transformed by said image transforming means as image information in each of said plurality of wavelength ranges; and signal processing means for processing signals of the image information of said observed image which is transformed and memorized by said memorizing means.

12. The frame sequential type imaging apparatus according to claim 5, wherein said frame sequential type imaging apparatus is an electronic endoscope.

13. The frame sequential type imaging apparatus according to any one of claims 1–3, wherein said observed image picked up by said image pick-up means is an observed image irradiated by reflected light from said object, the reflected light being emitted by said irradiating means, further comprising:

wavelength range separating means for separating said reflected light into light of said plurality of wavelength ranges and transmitting the light to said image forming position changing means.

14. The frame sequential type imaging apparatus according to claim 13, wherein said wavelength range separating means separates light in a specific wavelength range into multiple light, and said image forming position changing means forms an observed image irradiated by light in at least a part of said specific wavelength range separated by said wavelength range separating means in said offset position different from said same position.

15. The frame sequential type imaging apparatus according to any one of claims 1–3, wherein said irradiating means sequentially emits light of said plurality of wavelength ranges.

16. The frame sequential type imaging apparatus according to claim 15, wherein said observed image picked up by said image pick-up means is an observed image irradiated by reflected light originated from said object, said reflected light being emitted by said irradiating means, wavelength range separating means for separating light of a specific wavelength range in said plurality of wavelength ranges into multiple light is provided, and said image forming position changing means forms an observed image in at least a part of said specific wavelength range separated by said wavelength range separating means in said offset position different from said same position.

17. The frame sequential type imaging apparatus according to claim 16, where light of said plurality of wavelength ranges is a R light, G light, and B light and light of said specific wavelength range is a G light.

18. The frame sequential type imaging apparatus according to claim 16, further comprising:

memorizing means for memorizing said observed image picked up by said image picking up means as image information in each of said plurality of wavelength ranges; and signal processing means for processing signals of image information of said observed image memorized by said memorizing means.

19. The frame sequential type imaging apparatus according to claim 16, wherein said image forming position changing means includes three or more of a plurality of filters transmitting said reflected light and having different wavelength transmission characteristics, and said image forming position changing means forms said observed image having passed through at least two of said plurality of filters in said same position and forms said observed image having passed through at least one of remainder of said plurality of filters in said offset position different from said same position.

20. The frame sequential type imaging apparatus according to claim 16, wherein said image forming position changing means is a prism reflecting said reflected light and including a plurality of reflecting surfaces having different reflecting characteristics depending on wavelength ranges.

21. The frame sequential type imaging apparatus according to claim 16, further comprising, for an observed image formed in said image picking up means in one direction on rectangular coordinates on a surface lying at right angles to an optical axis of said reflected light, image transforming means for extending and compressing said observed image in a direction lying at right angles to said one direction to transform said observed image.

22. The frame sequential type imaging apparatus according to claim 16, wherein said frame sequential type imaging apparatus is an electronic endoscope.

23. The frame sequential type imaging apparatus according to any one of claims 1–3, wherein said observed image pickup up by said image pick-up means is an observed image irradiated by transmitted light having passed through said object, the transmitted light being emitted by said irradiating means, further comprising:

wavelength range separating means for separating light emitted by said irradiating means into the light of said plurality of wavelength ranges and irradiating the light on said object.

24. The frame sequential type imaging apparatus according to claim 23, wherein said wavelength range separating means separates light of a specific wavelength range into multiple light, and said image forming position changing means forms an observed image irradiated by light in at least a part of said specific wavelength range separated by said wavelength range separating means in said offset position different from said same position.

25. The frame sequential type imaging apparatus according to claim 24, wherein light of said plurality of wavelength ranges is a R light, G light, and B light and light of said specific wavelength range is a G light.

26. The frame sequential type imaging apparatus according to claim 24, further comprising:

memorizing means for memorizing said observed image picked up by said image picking up means as image information in each of said plurality of wavelength ranges, and signal processing means for processing signals of image information of said observed image memorized by said memorizing means.

27. The frame sequential type imaging apparatus according to claim 24, wherein said image forming position changing means includes three or more of a plurality of filters transmitting said transmitted light and having different wavelength transmission characteristics, and said image forming position changing means forms said observed image having passed through at least two of said plurality of filters in said same position and forms said observed image having passed through at least one of remainder of said plurality of filters in said offset position different from said same position.

28. The frame sequential type imaging apparatus according to claim 24, wherein said image forming position changing means comprises a prism reflecting said reflected light and including a plurality of reflecting surfaces having different reflecting characteristics depending on wavelength ranges.

29. The frame sequential type imaging apparatus according to claim 24, further comprising, for an observed image formed in said image pick-up means in one direction of rectangular coordinates on a surface lying at right angles to an optical axis of said reflected light, image transforming means for extending and compressing said observed image in a direction lying at right angles to said one direction to transform said observed image.

30. The frame sequential type imaging apparatus according to claim 29, further comprising:

memorizing means for memorizing said observed image picked up by said image pick-up means and transformed by said image transforming means as image information in each of said plurality of wavelength ranges, and signal processing means for processing signals of the image information of said observed image which is transformed and memorized by said memorizing means.

31. The frame sequential type imaging apparatus according to claim 30 wherein said signal processing means for restoring and processing the image information of said observed image which is transformed and memorized by said memorizing means.

32. The frame sequential type imaging apparatus according to claim 24, wherein said frame sequential type imaging apparatus comprises a microscope apparatus.

33. The frame sequential type imaging apparatus according to any one of claims 1–3, wherein said observed image picked up by said image pick-up means is an observed image irradiated by transmitted light having passed through said object, the transmitted light being emitted by said irradiating means, further comprising:

wavelength range separating means for separating said transmitted light into light of said plurality of wavelength ranges and transmitting the light to said image forming position changing means.

34. The frame sequential type imaging apparatus according to claim 33, wherein said wavelength range separating means separates light of a specific wavelength range into multiple light, and said image forming position changing means forms an observed image irradiated by light in at least a part of said specific wavelength range separated by said wavelength range separating means in said offset position different from said same position.

35. The frame sequential type imaging apparatus according to any one of claims 1–3, wherein said irradiating means sequentially emits light of said plurality of wavelength ranges.

36. The frame sequential type imaging apparatus according to claim 35, wherein said observed image picked up by said image pick-up means is an observed image irradiated by transmitted light having passed through said object, said transmitted light being emitted by said irradiating means, wavelength range separating means for separating light of a specific wavelength range in said plurality of wavelength ranges into multiple light is provided, and said image forming position changing means forms an observed image of at least a part of said specific wavelength range separated by said wavelength range separating means in said offset position different from said same position.

37. The frame sequential type imaging apparatus according to claim 36, wherein light of said plurality of wavelength ranges in a R light, G light, and B light and light of said specific wavelength range is a G light.

38. The frame sequential type imaging apparatus according to claim 36, further comprising:

memorizing means for memorizing said observed image picked up by said image picking up means as image information in each of said plurality of wavelength ranges, and signal processing means for processing signals of image information of said observed image memorized by said memorizing means.

39. The frame sequential type imaging apparatus according to claim 36, wherein said image forming position changing means includes three or more of a plurality of filters transmitting said transmitted light and having different wavelength transmission characteristics, and said image forming position changing means forms said observed image having passed through at least two of said plurality of filters in said same position and forms said observed image having passed through at least one of remainder of said plurality of filters in said offset position different from said same position.

40. The frame sequential type imaging apparatus according to claim 36, wherein said image forming position changing means is a prism reflecting said reflected light and including a plurality of reflecting surfaces having different reflecting characteristics depending on wavelength ranges.

41. The frame sequential type imaging apparatus according to claim 36, further comprising, for an observed image formed in said image picking up means in one direction of rectangular coordinates on a surface lying at right angles to an optical axis of said reflected light, image transforming means for extending and compressing said observed image in a direction lying at right angles to said one direction to transform said observed image.

42. The frame sequential type imaging apparatus according to claim 36, wherein said frame sequential type imaging apparatus is a microscope apparatus.

43. An image pick-up system including said frame sequential type imaging apparatus according to claim 1, comprising:

A/D converting means for A/D-converting signals of said observed image, picked up by said image pick-up means, in said plurality of wavelength ranges and producing image information;

memorizing means for memorizing said image information in said plurality of wavelength ranges by said A/D converting means;

controlling means for reading out said image information from said memorizing means by predetermined control;

D/A converting means for D/A-converting image information read out by said controlling means and producing video signals; and displaying means for inputting said video signals and displaying said observed image with higher resolution than the resolution of said imaging means.

* * * * *